(12) United States Patent
Zheleznyak

(10) Patent No.: US 12,174,459 B2
(45) Date of Patent: Dec. 24, 2024

(54) OPTIMIZED MULTIFOCAL WAVEFRONTS FOR PRESBYOPIA CORRECTION

(71) Applicant: Clerio Vision, Inc., Rochester, NY (US)

(72) Inventor: Leonard Zheleznyak, Pittsford, NY (US)

(73) Assignee: Clerio Vision, Inc., Rochester, NY (US)

( * ) Notice: Subject to any disclaimer, the term of this patent is extended or adjusted under 35 U.S.C. 154(b) by 0 days.

(21) Appl. No.: 18/226,068

(22) Filed: Jul. 25, 2023

(65) Prior Publication Data
US 2023/0367138 A1    Nov. 16, 2023

Related U.S. Application Data

(63) Continuation of application No. 17/369,273, filed on Jul. 7, 2021, now Pat. No. 11,747,650.
(Continued)

(51) Int. Cl.
G02C 7/02    (2006.01)
(52) U.S. Cl.
CPC .................... G02C 7/022 (2013.01)
(58) Field of Classification Search
CPC .......... G02C 7/022; G02C 7/042; G02C 7/06; G02C 2202/20
(Continued)

(56) References Cited

U.S. PATENT DOCUMENTS 5,849,006 A   12/1998  Frey et al.
6,261,220 B1   7/2001  Frey et al.
(Continued)

FOREIGN PATENT DOCUMENTS

WO    2008002796 A2   1/2008
WO    2009143054 A2  11/2009
(Continued)

OTHER PUBLICATIONS

Flitcroft et al., "IMI—Defining and Classifying Myopia: A Proposed Set of Standards for Clinical and Epidemiologic Studies", Investigative Ophthalmology & Visual Science, vol. 60, No. 3, Feb. 2019, pp. M20-M30.
(Continued)

*Primary Examiner* — William R Alexander
(74) *Attorney, Agent, or Firm* — Kilpatrick Townsend & Stockton LLP

(57) ABSTRACT

Example embodiments include methods of modifying a lens to improve image quality of a patient with presbyopia A method includes inducing changes in refractive index of subsurface volumes of the lens to form a first subsurface optical structure and a second subsurface optical structure. The first subsurface optical structure is configured to induce a first wavefront correction configured to increase depth of focus and intermediate vision quality for a patient when the patient has a first range of accommodation. The first subsurface optical structure and the second subsurface optical structure, in combination, are configured to induce a second wavefront correction configured to increase depth of focus and intermediate vision quality for the patient when the patient has a second range of accommodation less than the first range of accommodation.

18 Claims, 26 Drawing Sheets

Related U.S. Application Data

(60) Provisional application No. 63/049,277, filed on Jul. 8, 2020.

(58) Field of Classification Search
USPC .................................................. 351/159.74
See application file for complete search history.

(56) References Cited

U.S. PATENT DOCUMENTS

| | | | |
|---|---|---|---|
| 6,271,914 | B1 | 8/2001 | Frey et al. |
| 6,720,221 | B1 | 4/2004 | Ahn et al. |
| 7,789,910 | B2 | 9/2010 | Knox et al. |
| 8,337,553 | B2 | 12/2012 | Knox et al. |
| 8,512,320 | B1 | 8/2013 | Knox et al. |
| 8,617,147 | B2 | 12/2013 | Knox et al. |
| 8,901,190 | B2 | 12/2014 | Smith et al. |
| 8,932,352 | B2 | 1/2015 | Knox et al. |
| 9,060,847 | B2 | 6/2015 | Smith et al. |
| 9,144,491 | B2 | 9/2015 | Knox et al. |
| 9,492,323 | B2 | 11/2016 | Knox et al. |
| 9,545,340 | B1 | 1/2017 | Knox et al. |
| 9,622,912 | B2 | 4/2017 | Knox et al. |
| 9,939,558 | B2 | 4/2018 | Knox et al. |
| 10,226,381 | B2 | 3/2019 | Knox et al. |
| 2005/0187622 | A1 | 8/2005 | Sandstedt et al. |
| 2007/0052920 | A1* | 3/2007 | Stewart ............... G02C 7/083 351/159.44 |
| 2008/0001320 | A1 | 1/2008 | Knox et al. |
| 2010/0066973 | A1 | 3/2010 | Portney |
| 2010/0321635 | A1 | 12/2010 | Apter et al. |
| 2012/0081661 | A1 | 4/2012 | Yamakaji |
| 2012/0310223 | A1 | 12/2012 | Knox et al. |
| 2013/0114128 | A1* | 5/2013 | Haddock ............... G02C 7/083 359/569 |
| 2013/0178934 | A1 | 7/2013 | Knox et al. |
| 2013/0226162 | A1 | 8/2013 | Knox et al. |
| 2013/0324983 | A1 | 12/2013 | Liang |
| 2015/0277150 | A1 | 10/2015 | Granger et al. |
| 2015/0351901 | A1* | 12/2015 | Stoy ................... A61F 2/1648 623/6.34 |
| 2016/0054195 | A1 | 2/2016 | Greivenkamp, Jr. et al. |
| 2016/0144580 | A1 | 5/2016 | Knox et al. |
| 2016/0296662 | A1* | 10/2016 | Stoy ..................... A61L 27/52 |
| 2017/0035613 | A1 | 2/2017 | Knox et al. |
| 2017/0108711 | A1 | 4/2017 | Muschielok et al. |
| 2017/0119581 | A1 | 5/2017 | Gray et al. |
| 2017/0146820 | A1 | 5/2017 | Brennan et al. |
| 2017/0176772 | A1 | 6/2017 | Bakaraju et al. |
| 2017/0181846 | A1 | 6/2017 | Knox et al. |
| 2018/0021172 | A1 | 1/2018 | Zheleznyak et al. |
| 2018/0132996 | A1 | 5/2018 | Tiwari et al. |
| 2018/0206979 | A1 | 7/2018 | Knox et al. |
| 2018/0231696 | A1 | 8/2018 | Knox et al. |
| 2018/0243082 | A1 | 8/2018 | Zheleznyak et al. |
| 2018/0373060 | A1 | 12/2018 | Knox et al. |
| 2019/0046357 | A1 | 2/2019 | Knox et al. |
| 2019/0110889 | A1 | 4/2019 | Bor et al. |
| 2019/0235279 | A1* | 8/2019 | Hones ..................... G02C 7/10 |
| 2019/0343683 | A1 | 11/2019 | Zheleznyak et al. |
| 2020/0033666 | A1* | 1/2020 | Li ......................... G02C 7/083 |
| 2020/0038549 | A1* | 2/2020 | Stoy ..................... A61L 27/16 |
| 2020/0054485 | A1 | 2/2020 | Knox |
| 2020/0310159 | A1 | 10/2020 | Zhang |
| 2021/0018762 | A1 | 1/2021 | Zheleznyak |
| 2021/0165244 | A1* | 6/2021 | Hones ..................... G02C 7/10 |
| 2021/0294123 | A1 | 9/2021 | Weeber et al. |
| 2022/0171214 | A1 | 6/2022 | Weeber et al. |

FOREIGN PATENT DOCUMENTS

| | | |
|---|---|---|
| WO | 2012166696 A1 | 12/2012 |
| WO | 2015006274 A1 | 1/2015 |
| WO | 2017106321 A1 | 6/2017 |
| WO | 2018182946 A1 | 10/2018 |
| WO | 2019010345 A1 | 1/2019 |
| WO | 2019147952 A1 | 8/2019 |
| WO | 2020102514 A1 | 5/2020 |
| WO | 2021108585 A1 | 6/2021 |
| WO | 2021202247 A1 | 10/2021 |

OTHER PUBLICATIONS

Hiraoka et al., "Relationships Between Higher-order Wavefront Aberrations and Natural Progression of Myopia in Schoolchildren", Scientific Reports, vol. 7, Article No. 7876, Aug. 11, 2017, 9 Pages.

Huang et al., "Efficacy Comparison of 16 Interventions for Myopia Control in Children", America Academy of Ophthalmology, vol. 123, No. 4, Apr. 2016, pp. 697-708.

Kim et al., "Improving Through-Focus Visual Performance Using Primary and Secondary Spherical Aberrations", ARVO Annual Meeting Abstract, Investigative Ophthalmology & Visual Science, vol. 53, 2012, 2 pp.

Li et al., "Studies Using Concentric Ring Bifocal and Peripheral Add Multifocal Contact Lenses to Slow Myopia Progression in School-Aged Children: A Meta-Analysis", Ophthalmic & Physiological Optics, vol. 37, No. 1, Jan. 2017, pp. 51-59.

Moreno et al., "Modulation Light Efficiency of Diffractive Lenses Displayed in a Restricted Phase-Mostly Modulation Display", Applied Optics, vol. 43, No. 34, Dec. 1, 2004, pp. 6278-6284.

Plaza-Puche et al., "Correlating Optical Bench Performance With Clinical Defocus Curves in Varifocal and Trifocal Intraocular Lenses", Journal of Refractive Surgery, vol. 31, No. 5, May 2015, pp. 300-307.

Resnikoff et al., "Myopia—A 21st Century Public Health Issue", Investigative Ophthalmology & Visual Science, vol. 60, No. 3, Feb. 2019, pp. Mi-Mii.

Savage et al., "First Demonstration of Ocular Refractive Change Using Blue-IRIS in Live Cats", Investigative Ophthalmology & Visual Science, vol. 55, No. 7, Jul. 1, 2014, pp. 4603-4612.

Si et al., "Orthokeratology for Myopia Control: A Meta-Analysis", Optometry and Vision Science, vol. 92, No. 3, Mar. 2015, pp. 252-257.

Smith et al., "Peripheral Vision Can Influence Eye Growth and Refractive Development in Infant Monkeys", Investigative Ophthalmology & Visual Science, vol. 46, No. 11, Nov. 2005, 16 Pages.

Tedja et al., "IMI—Myopia Genetics Report", Investigative Ophthalmology & Visual Science, vol. 60, No. 3, Feb. 2019, pp. M89-M105.

Troilo et al., "IMI—Report on Experimental Models of Emmetropization and Myopia", Investigative Ophthalmology & Visual Science, vol. 60, No. 3, Feb. 2019, pp. M31-M88.

Watson et al., "Predicting Visual Acuity From Wavefront Aberrations", Journal of Vision, vol. 8, No. 4, Apr. 22, 2008, pp. 1-19.

Wildsoet et al., "IMI—Interventions for Controlling Myopia Onset and Progression Report", Investigative Ophthalmology & Visual Science, vol. 60, No. 3, Feb. 2019, pp. M106-M131.

Wolffsohn et al., "IMI—Clinical Myopia Control Trials and Instrumentation Report", Investigative Ophthalmology & Visual Science, vol. 60, No. 3, Feb. 2019, pp. M132-M160.

Wolffsohn et al., "IMI—Myopia Control Reports Overview and Introduction", Investigative Ophthalmology & Visual Science, vol. 60, No. 3, Feb. 2019, pp. M1-M19.

Xu et al., "Noninvasive Intratissue Refractive Index Shaping (IRIS) of the Cornea with Blue Femtosecond Laser Light", Investigative Ophthalmology & Visual Science, vol. 52, No. 11, Oct. 17, 2011, pp. 8148-8155.

Zheleznyak et al., "Impact of Pupil Transmission Apodization on Presbyopic Through-Focus Visual Performance With Spherical Aberration", Investigative Ophthalmology & Visual Science, vol. 55, No. 1, Jan. 2014, pp. 70-77.

Zheleznyak et al., "Modified Monovision With Spherical Aberration to Improve Presbyopic Through-Focus Visual Performance", Investigative Ophthalmology & Visual Science, vol. 54, No. 5, May 2013, pp. 3157-3165.

(56) References Cited

OTHER PUBLICATIONS

Zheleznyak et al., "Optical and Neural Anisotropy in Peripheral Vision", Journal of Vision, vol. 16, No. 5, Mar. 2016, pp. 1-11.

* cited by examiner

| | Acc. Ability | Need |
|---|---|---|
| Early Presbyope | Up to 2 D | 1 D |
| Mid Presbyope | Up to 1 D | 2 D |
| Advanced Presbyope or Monofocal IOL | 0 D | 3 D |

Early Presbyope (<45yrs)

1 D bifocal
1.5 D bifocal
Pure SA shape
Pure SA LIRIC

Mid Presbyope (45-55yrs)

2 D bifocal
2 D bifocal + SA
1 and 2 D trifocal
1 and 2 D trifocal + SA

Adv Presbyope (>55yrs or IOL)

1.5 and 3 D trifocal
1.5 and 3 D trifocal + SA
2 D bifocal
2 D bifocal + SA
1 and 2 D trifocal
1 and 2 D trifocal + SA

```
Generate a first phase-wrapped wavefront
corresponding to a first optical structure
configured to cause the ophthalmic lens to
diffract light to multiple focal points, wherein
the first phase-wrapped wavefront is a
wavefront having a first predetermined
phase height less than 1 wave
```
— 2110

↓

```
Generate a first spherical wavefront
configured to cause a first spherical
aberration in the ophthalmic lens
```
— 2120

↓

```
Generate, based on the first phase-wrapped
wavefront and the first spherical wavefront,
energy output parameters for forming a first
subsurface optical structure in the
ophthalmic lens using an energy source,
wherein the first subsurface optical structure
is configured to correct presbyopia with an
extended depth of focus that allows for
increased intermediate vision quality.
```
— 2130

FIG. 21

OPTIMIZED MULTIFOCAL WAVEFRONTS FOR PRESBYOPIA CORRECTION

CROSS-REFERENCES TO RELATED APPLICATIONS

The present application is a Continuation of U.S. patent application Ser. No. 17/369,273 filed Jul. 7, 2021 (Allowed); which claims the benefit of U.S. Provisional Appln No. 63/049,277 filed Jul. 8, 2020, the disclosures which are incorporated herein by reference in their entirety for all purposes.

BACKGROUND

Optical aberrations that degrade visual acuity are common. Optical aberrations are imperfections of the eye that degrade focusing of light onto the retina. Common optical aberrations include lower-order aberrations (e.g., astigmatism, positive defocus (myopia) and negative defocus (hyperopia)) and higher-order aberrations (e.g., spherical aberrations, coma and trefoil).

Existing treatment options for correcting optical aberrations include glasses, contact lenses, and reshaping of the cornea via laser eye surgery. Additionally, intraocular lenses are often implanted to replace native lenses removed during cataract surgery.

Presbyopia may be defined as a gradual loss of near vision, or the ability to focus on nearby objects, that may occur naturally with age. Presbyopia may become noticeable for patients in their early to mid-40s and may continue to worsen over time as they age until around age 65. As patients age, the crystalline lens gradually stiffens and grows in size, generally making it difficult for the lens to accommodate (or change shape) adequately to focus on nearby objects.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments described herein are directed to ophthalmic lenses having at least one subsurface optical structure (e.g., diffractive optical structures and/or non-diffractive optical structures) with enhanced distribution of refractive index values. In many embodiments, the subsurface refractive index variations are formed via focusing femtosecond duration laser pulses onto a targeted sequence of subsurface volumes of an ophthalmic lens. The refractive indexes of the annular optical structure vary radially relative to the optical axis up to an upper limit refractive index (e.g., providing any suitable phase change less than 1.0 wave). The refractive indexes of the annular optical structure are equal to the upper limit refractive index over a range of radii (e.g., at least 0.15 mm length) from the optical axis. In many embodiments, the refractive indexes of the annular optical structure are equal to a lower limit refractive index (e.g., providing a phase change of 0.0 waves) over a range of radii (e.g., at least 0.15 mm length) from the optical axis. The enhanced distribution of refractive index values can be formed using fewer laser pulses in comparison with a corresponding distribution of refractive index values determined via a ratio approach. Additionally, limiting the refractive index values to equal to or less than the upper limit refractive index helps to reduce damage induced by the sequence of laser pulses at a given pulse energy level as compared to forming a corresponding subsurface optical structure(s) using refractive index values that are greater than the upper limit refractive index. The approaches described herein may be useful in forming a subsurface optical structure(s) in any suitable ophthalmic lenses (e.g., intraocular lenses, contact lenses, corneas, glasses, and/or native lenses).

In some embodiments, methods, systems, and devices are described for determining parameters for forming an optical structure (e.g., a subsurface optical structure) in an ophthalmic lens for improving vision in a patient. These parameters may be used to control an energy source to appropriately form the desired optical structure.

In many cases, presbyopia patients less than 45 years old may be classified as early presbyopes requiring relatively minor correction; presbyopia patients between 45 and 55 years old may be classified as mid presbyopes requiring a moderate level of correction; and presbyopia patients over the age of 55 years old (or patients who have received a non-accommodating manner focal intraocular lens (IOL)) may be classified as advanced presbyopes requiring a relatively large level of correction.

Disclosed herein are methods for forming subsurface optical structures in an ophthalmic lens for improving patient vision (e.g., for correcting presbyopia). In some embodiments, the method includes defining a first phase-wrapped wavefront corresponding to a first optical structure configured to cause the ophthalmic lens to diffract light to multiple focal points, wherein the first phase-wrapped wavefront is a wavefront having a first predetermined phase height (e.g., not equal to 1 wave); defining a first spherical wavefront configured for inducing a first spherical aberration in the ophthalmic lens; and generating, based on the first phase-wrapped wavefront and the first spherical wavefront, energy output parameters for forming a first subsurface optical structure in the ophthalmic lens using an energy source, wherein the first subsurface optical structure is configured to correct presbyopia by providing extended depth of focus that produces increased intermediate vision quality.

In some embodiments, the method may include accessing an optical prescription for the patient, wherein the optical prescription comprises one or more prescription parameters for refracting light directed at a retina of the patient so as to improve vision; and generating a first variable wavefront based on the optical prescription, wherein the first variable wavefront comprises at least one portion that has a phase height greater than 1 wave; wherein generating the first phase-wrapped wavefront comprises collapsing the first variable wavefront to the first predetermined phase height.

In some embodiments, the energy output parameters specify a plurality of power levels corresponding to a plurality of optical zones on the ophthalmic lens. The method may include directing a first energy beam from the energy source at a first subsurface optical zone of the ophthalmic lens for a first duration, wherein a power level of the first energy beam is based on a corresponding power level as specified by the energy output parameters; and directing a second energy beam from the energy source at a second subsurface optical zone on the ophthalmic lens for a second duration, wherein a power level of the second energy beam is based on a corresponding power level as specified by the energy output parameters. The first energy beam and the second energy beam may alter refractive indexes of the first subsurface optical zone and the second subsurface optical zone, respectively, and wherein the first subsurface optical structure comprises the first subsurface optical zone and the second subsurface optical zone.

In some embodiments, the first optical structure is configured to cause the ophthalmic lens to be a bifocal lens having a 2 diopter add power. In some embodiments, the first optical structure is configured to cause the ophthalmic lens to be a bifocal lens having a 1.5 diopter add power. In some embodiments, the first predetermined phase height is between about 0.5 to 0.6 waves. In some embodiments, the first spherical aberration is around −0.2 μm. In some embodiments, the first spherical aberration is around 0.2 μm.

In some embodiments, forming the subsurface optical structure comprises directing an energy beam toward a volume of the ophthalmic lens so as to change a refractive index of the volume.

In some embodiments, the method may include defining a second phase-wrapped wavefront corresponds to a second optical structure configured to cause the ophthalmic lens to diffract light to multiple focal points, wherein the second phase-wrapped wavefront is a wavefront having a second predetermined phase height (e.g., not equal to 1 wave); defining a second spherical wavefront configured to cause a second spherical aberration in the ophthalmic lens; and generating, based on the second phase-wrapped wavefront and the second spherical wavefront, energy output parameters for forming a second subsurface optical structure in the ophthalmic lens using an energy source. In some embodiments, the first subsurface optical structure is configured to correct a first stage of presbyopia in the patient, the second subsurface optical structure is configured to correct a second stage of presbyopia in the patient, and the second stage of presbyopia in the patient is later than the first stage of presbyopia in the patient.

Also disclosed are of ophthalmic lenses for improving vision (e.g., for correcting presbyopia in a patient), which may in some embodiments be performed using the described methods. In some embodiments an ophthalmic lens may include a first subsurface optical structure comprising concentric Fresnel rings within an interior of the ophthalmic lens. Each of the concentric Fresnel rings can define a volume having a desired refractive index. The first subsurface optical structure may be configured to: induce a first spherical aberration in the ophthalmic lens; and diffract light to multiple focal points based on a phase-wrapped wavefront having a first predetermined phase height (e.g., not equal to 1 wave).

In some embodiments, the ophthalmic lens is an intraocular lens, a contact lens, or a cornea of the patient. In some embodiments, wherein the first subsurface optical structure is configured to cause the ophthalmic lens to be a bifocal lens having a 2 diopter add power. In some embodiments, the first subsurface optical structure is configured to cause the ophthalmic lens to be a bifocal lens having a 1.5 diopter add power. In some embodiments, the first predetermined phase height is between about 0.5 to 0.6 waves. In some embodiments, the first spherical aberration is around −0.2 μm. In some embodiments, the first spherical aberration is around 0.2 μm In some embodiments, the ophthalmic lens includes a second subsurface optical structure. The first subsurface optical structure can be embedded in a first layer of the ophthalmic lens. The second subsurface optical structure can be embedded in a second layer of the ophthalmic lens. In some embodiments, the first subsurface optical structure is configured to correct a first stage of presbyopia in the patient and the second subsurface optical structure is configured to correct a second stage of presbyopia in the patient. The second stage of presbyopia in the patient can be later than the first stage of presbyopia in the patient.

BRIEF DESCRIPTION OF THE DRAWINGS

FIG. 20 is a table showing example wavefronts that may be implemented for different stages of presbyopia.

FIG. 21 illustrates an example method 2000 for forming a subsurface optical structure in an ophthalmic lens for correcting presbyopia in a patient.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
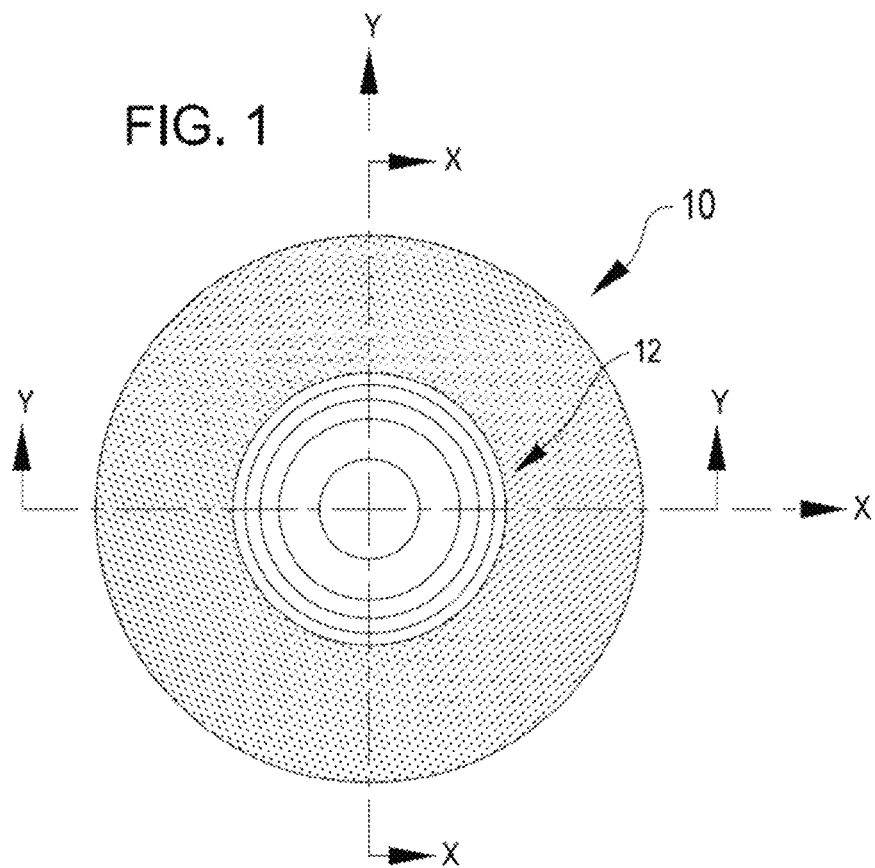
FIG. 1 is a plan view illustration of an ophthalmic lens that includes subsurface optical structures with enhanced distribution of refractive index variations, in accordance with embodiments.

FIG. 1 is a plan view illustration of an ophthalmic lens 10 that includes one or more subsurface optical structures 12 with annular distribution of refractive index variations, in accordance with embodiments. The one or more subsurface structures 12 described herein can be formed in any suitable type of ophthalmic lens including, but not limited to, intraocular lenses, contact lenses, corneas, spectacle lenses, and native lenses (e.g., a human native lens). The one or more subsurface optical structures 12 with annular distribution of refractive index variations can be configured to provide a suitable refractive correction for each of many optical aberrations such as astigmatism, myopia, hyperopia, spherical aberrations, coma and trefoil, as well as any suitable combination thereof.

Figure 2:
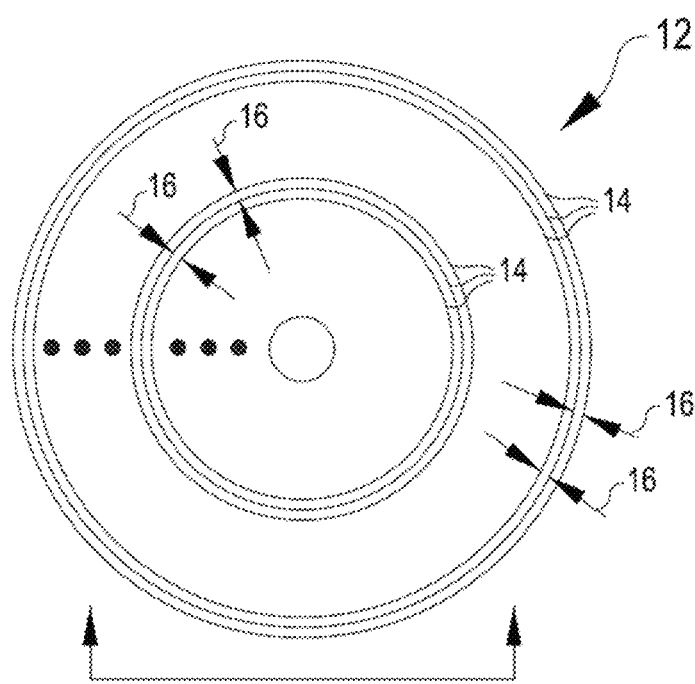
FIG. 2 is a plan view illustration of a layer of the subsurface optical structures of the ophthalmic lens of FIG. 1.

FIG. 2 is a plan view illustration of one of the subsurface optical structures 12 of the ophthalmic lens 10. The illustrated subsurface optical structure 12 includes concentric circular sub-structures 14 separated by intervening line spaces or gaps 16. In FIG. 2, the size of the intervening line spaces 16 is shown much larger than in many actual embodiments. For example, example embodiments described herein have an outer diameter of the concentric circular sub-structures 14 of 3.75 mm and intervening line spaces 16 of 0.25 um, thereby having 1,875 of the concentric circular sub-structures 14 in embodiments where the concentric circular substructures 14 extend to the center of the subsurface optical structure 12. Each of the concentric circular sub-structures 14 can be formed by focusing suitable laser pulses onto contiguous sub-volumes of the ophthalmic lens 10 so as to induce changes in refractive index of the sub-volumes so that each of the sub-volumes has a respective refractive index different from an adjacent portion of the ophthalmic lens 10 that surrounds the sub-structure 14 and is not part of any of the subsurface optical structures 12.

In many embodiments, a refractive index change is defined for each sub-volume of the ophthalmic lens 10 that form the subsurface optical structures 12 so that the resulting subsurface optical structures 12 would provide a desired optical correction when formed within the ophthalmic lens 10. The defined refractive index changes are then used to determine parameters (e.g., laser pulse power (mW), laser pulse width (fs)) of laser pulses that are focused onto the respective sub-volumes to induce the desired refractive index changes in the sub-volumes of the ophthalmic lens 10.

While the sub-structures 14 of the subsurface optical structures 12 have a circular shape in the illustrated embodiment, the sub-structures 14 can have any suitable shape and distribution of refractive index variations. For example, a single sub-structure 14 having an overlapping spiral shape can be employed. In general, one or more substructures 14 having any suitable shapes can be distributed with intervening spaces so as to provide a desired diffraction of light incident on the subsurface optical structure 12ss. More information about subsurface optical structures and forming such structures may be found in U.S. Provisional Application No. 63/001,993, which is incorporated herein by reference in its entirety for all purposes.

In some embodiments, a system including one or more processors may be configured to determine parameters for forming one or more optical structures (e.g., subsurface optical structures) for improving or correcting vision. In some embodiments, the one or more processors of the system may be configured to access a first optical prescription for the patient. The first optical prescription may be prescribed by, for example, an optometrist. The first optical prescription may include one or more prescription parameters for refracting light directed at a retina of the patient so as to improve vision. The prescription parameters may be determined based on any suitable means of measurement. The prescription parameters may specify any suitable parameters for correcting or improving vision. For example, the prescription parameters may include diopter values of sphere, cylinder, or axis. The prescription parameters may include parameters for correcting one or more of a variety of low-order aberrations (e.g., myopia, hyperopia, astigmatism) and high-order aberrations (e.g., spherical aberration, coma, trefoil).

Figure 3A:
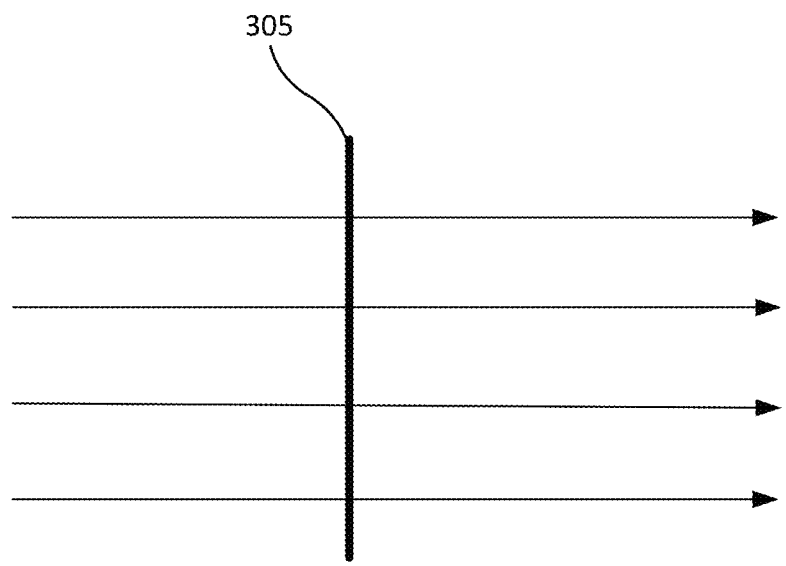
FIGS. 3A-3B illustrate example wavefronts through a medium for parallel and converging rays of light.
Figure 3B:
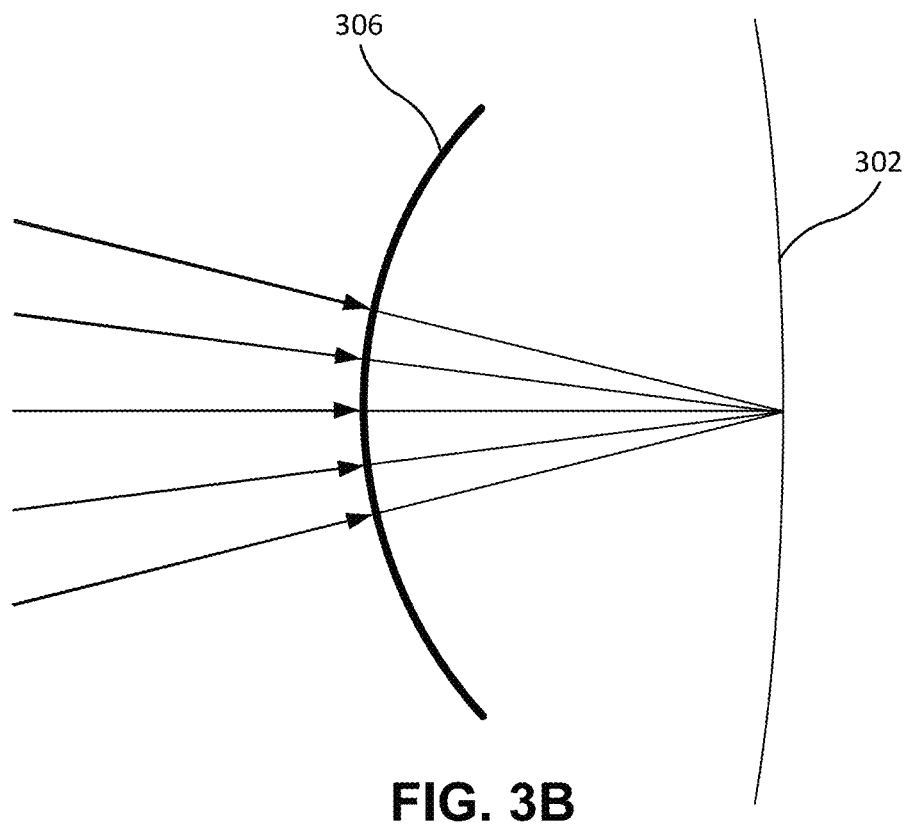

FIGS. 3A-3B illustrate example wavefronts 305, 306 through a medium for parallel and converging rays of light. Prescriptions for correcting or improving vision of a patient can essentially be described as a prescription for creating an optical structure that effects a wavefront configured to modify incoming rays of light before they reach the retina of the patient. A wavefront is an imaginary surface of constant phase. A wavefront can also be thought of as a surface that is normal or perpendicular to rays of light passing through the wavefront. FIG. 3A illustrates a planar wavefront 305 from parallel rays of light. As is evident, the wavefront 305 is perpendicular to the parallel rays of light at each point of intersection. FIG. 3B illustrates a spherical wavefront 306 from converging rays of light. FIG. 3B simulates an ideal configuration of an eye, where the rays of light converge at a single point (on the retina 302). Each of the rays is perpendicular to the wavefront 307 at its respective point of intersection with the wavefront 307. The illustrated rays converge at a single point.

Figure 3C:
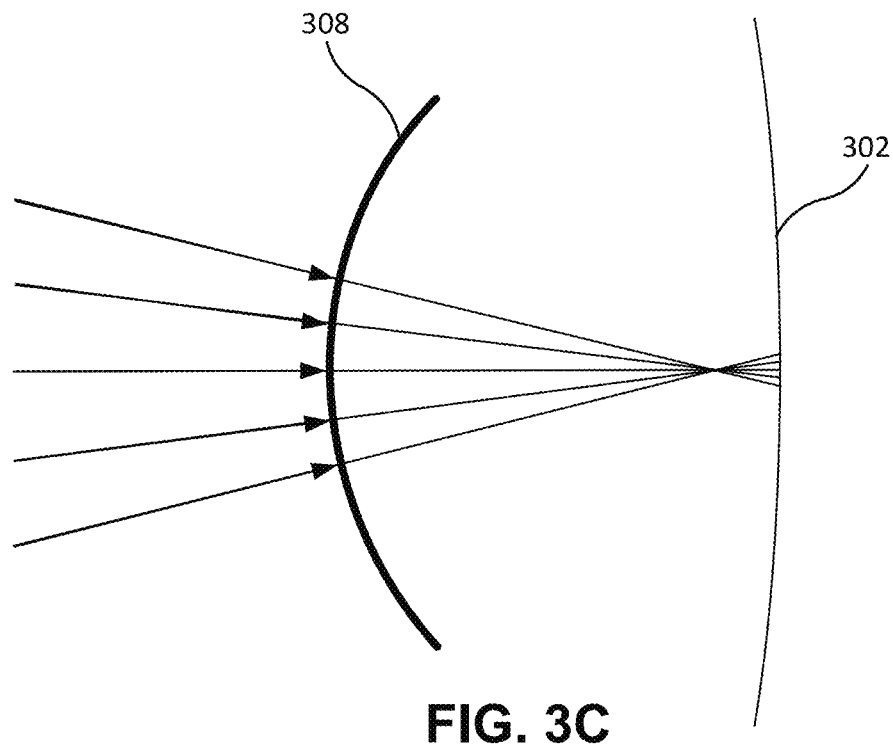
FIGS. 3C-3D illustrate example wavefronts that may simulate aberrations of the eye.
Figure 3D:
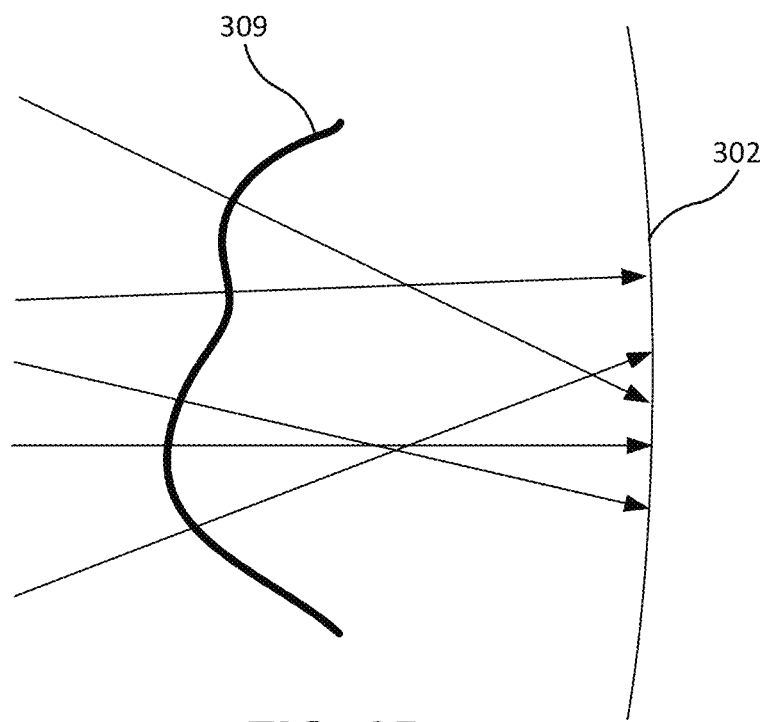

FIGS. 3C-3D illustrate example wavefronts 308, 309 that may simulate aberrations of the eye. Unlike the rays in FIG. 3B, the rays in FIG. 3C do not converge at a single point on the retina 302 (e.g., at or near the macula). Such non-convergence may cause issues with vision by not allowing for a focused image (e.g., causing myopia). FIG. 3D illustrates an aberrated wavefront 309 simulating another aberration of the eye (e.g. higher order aberrations). Again, each of the rays is perpendicular to the wavefront 309 at its respective point of intersection with the wavefront 309. And again, as illustrated, the rays in FIG. 3D do not converge at a single point on the retina 302 (and in fact do not converge at all), causing issues with vision. An appropriate optical structure with a corrective wavefront may be used to correct issues produced by aberrations by, for example, refracting light such that the light rays are made to converge at a single appropriate point on the retina 302. Disclosed herein are methods, devices, and systems for use in forming such optical structures. Although the disclosure focuses on methods, devices, and systems for correcting aberrations of the eye, the disclosure also contemplates enhancing what may be considered normal vision by similar methods, devices, and systems.

Figure 3E:
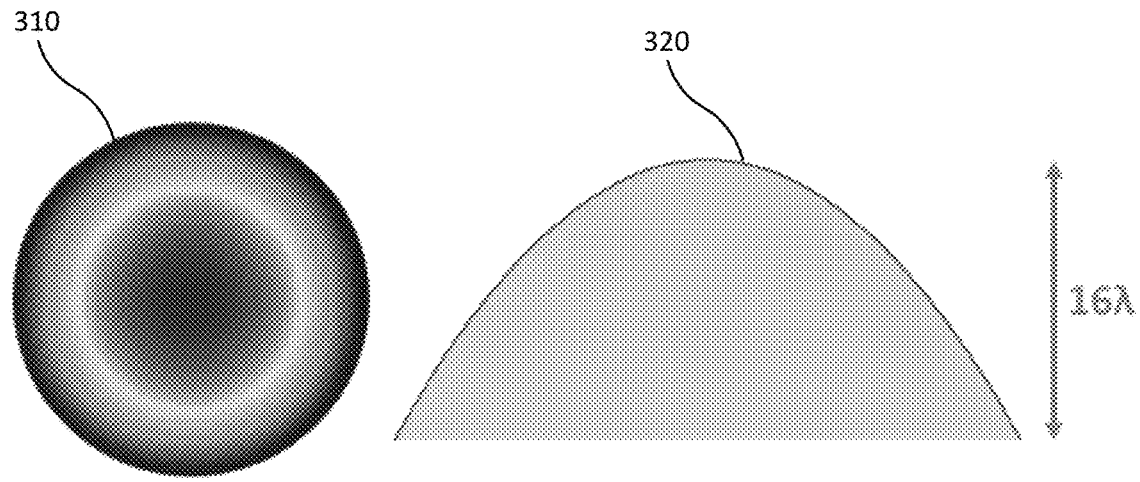
FIG. 3E illustrates a two-dimensional wavefront map and a corresponding first variable wavefront.

FIG. 3E illustrates a two-dimensional wavefront map 310 and a corresponding first variable wavefront 320. In some embodiments, the one or more processors may use the first optical prescription to determine a wavefront for an optical structure for correcting or improving vision of the patient. In some embodiments, the one or more processors may generate a wavefront map, which may be visualized, for example, by the two-dimensional wavefront map 310. The contours of the two-dimensional wavefront map 310 may specify different optical phases of the corresponding wavefront. For example, the different shades in the two-dimensional wavefront map 310 specifies different optical phases of the corresponding wavefront. In some embodiments, the one or more processors may do so by first computing the Zernike coefficient for defocus ($C_{2,0}$) using the following equation:

$$C_{2,0} = P \cdot r_{max}^2/(4 \cdot \mathrm{sqrt}(3)), \text{ where } P \text{ is an add power specified in the first prescription, and } r_{max} \text{ is the maximum radius of an optical zone.} \quad (1)$$

The Zernike coefficient is a scalar that may be expressed in units of micrometers. In some embodiments, the two-dimensional wavefront map may then be calculated using the following equation:

$$W_{um} = C_{2,0} \cdot \mathrm{sqrt}(3) \cdot (2 \cdot \rho^2 - 1), \text{ where } \rho \text{ is a normalized radial pupil coordinate (radial coordinate/} r_{max}) \quad (2)$$

$W_{um}$ provides a value (e.g., in units of micrometers) for each point of a two-dimensional wavefront map. Referencing FIG. 3D, the two-dimensional wavefront map 310 for a particular optical prescription may be generated using this equation.

In some embodiments, the one or more processors may be configured to generate a first variable wavefront based on the first optical prescription. Referencing FIG. 3D, for example, the first variable wavefront 320 may be generated based on specifications provided by the first optical prescription. The first variable wavefront describes a wavefront in units of waves with respect to a specified wavelength. In some embodiments, the first variable wavefront comprises at least one portion that has a phase height greater than 1 wave. In some embodiments, the first variable wavefront may be generated based on the two-dimensional wavefront map. The first variable wavefront may be determined with respect to any desired wavelength by dividing $W_{um}$ for each point by the desired wavelength. For example, the first variable wavefront may be determined with respect to a center of the visible spectrum (e.g., 0.555 μm in daylight). In this example, the equation below may be used to generate a first variable wavefront at 0.555 μm).

$$W_{wv} = W_{um}/0.555 \text{ μm} \quad (3)$$

Figure 3F:
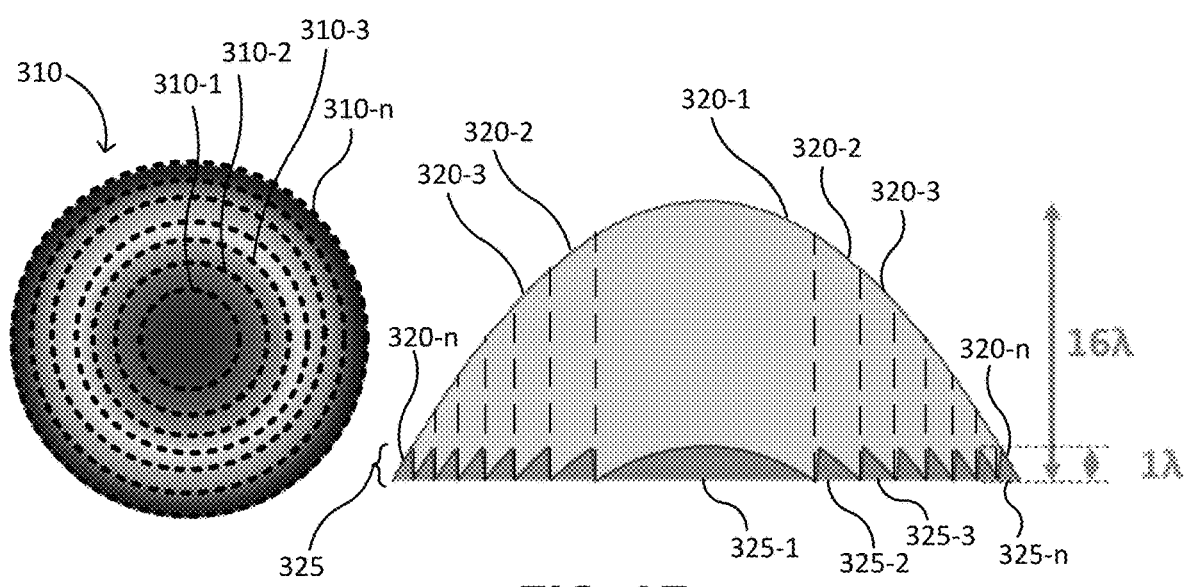
FIG. 3F illustrates a first phase-wrapped wavefront corresponding to the first variable wavefront.

FIG. 3F illustrates a first phase-wrapped wavefront 325 corresponding to the first variable wavefront 320. In some embodiments, the one or more processors may be configured to phase wrap the first variable wavefront, which may include collapsing the first variable wavefront to generate a first phase-wrapped wavefront. Phase wrapping the first variable wavefront may involve collapsing the first variable wavefront into a wavefront having a predetermined phase height (i.e., the height from peak to valley of the wavefront). For example, referencing FIG. 3B, the first phase-wrapped wavefront 325 may have a phase height of 1 wave. Phase-wrapping a variable wavefront to 1 wave causes no appreciable change in diffraction or refraction of light rays, and may thus be suitable, for example, for a patient having only myopia. An example Matlab algorithm for phase-wrapping to a phase height of 1 wave is shown below, where W555=$W_{wv}$ and Wrap=1:

```
while cnt == 0
  W555( W555 < -Wrap ) = W555( W555 < -Wrap ) + Wrap;
  if sum( W555(:) < -Wrap ) == 0
    cnt = 1;
  end
end
cnt = 0;
while cnt == 0
  W555( W555 > Wrap ) = W555( W555 > Wrap ) - Wrap;
  if sum( W555(:) > Wrap ) == 0
    cnt = 1;
  end
end
```

In some embodiments, collapsing the first variable wavefront may include identifying a plurality of discrete segments of the first variable wavefront. In some embodiments, as is the case in FIG. 3F, each of these discrete segments (e.g., 320-1 to 320-n) may be circumferential discrete segments that extend radially around the two-dimensional wavefront map 310 of the ophthalmic lens. For example, the discrete segment 320-1 in the first variable wavefront 320 may correspond to the portion 310-1 in the two-dimensional wavefront 310, the discrete segment 320-2 may correspond to the segment 310-2, the discrete segment 320-3 may correspond to the segment 310-3, and so on. In other embodiments, the discrete segments may not be circumferential, and the first variable wavefront may be segmented based on, for example, phase height. In the example illustrated in FIG. 3F, each of the discrete segments (325-1 to 325-n) is circumferential, and each discrete segment is adjacent to and concentric with another discrete segment. For example, the discrete segment 325-2 is adjacent to and concentric with the discrete segment 325-1 (similarly, the discrete segment 325-3 is adjacent to and concentric with the discrete segment 325-2, and so on). In some embodiments, the one or more processors of the system may reduce a phase height of each discrete segment by a respective scalar such that a peak of the first discrete segment is at a desired phase height. For example, in FIG. 3F, the phase height of each discrete segment is reduced to a predetermined phase height of 1 wave, yielding the first phase-wrapped wavefront 325. As mentioned above, collapsing the first variable wavefront 320 to the phase-wrapped wavefront 325 (which is collapsed to 1 wave) causes no appreciable change in diffraction or refraction, and light rays passing an optical structure based on the collapsed phase-wrapped wavefront 325 essentially behave in the same manner as light rays passing an optical structure formed based on the first variable wavefront 320. The resulting phase-wrapped wavefront may include a central discrete segment (e.g., the discrete segment 325-1) and a number of surrounding circumferential, adjacent echelettes (e.g., the discrete segments 325-2 to 325-n) as illustrated in FIG. 3E.

Figure 4:
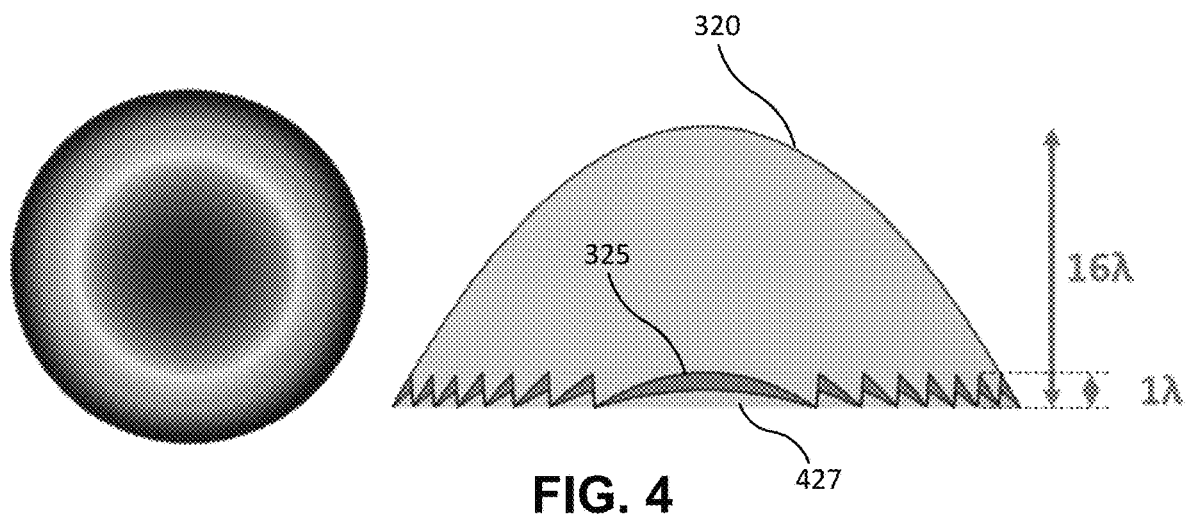
FIG. 4 illustrates a second phase-wrapped wavefront having a phase height less than 1 wave.

FIG. 4 illustrates a second phase-wrapped wavefront 427 having a phase height less than 1 wave. In some embodiments, the system may be configured to phase wrap the first variable wavefront at a predetermined phase height that is not at 1 wave to generate a second phase-wrapped wavefront. For example, referencing FIG. 5, the predetermined phase height of the illustrated phase-wrapped wavefront 427 is less than 1 wave. As discussed further below, collapsing a wavefront to a phase height other than 1 wave causes diffraction, which may be useful for creating a multifocal optical structure. Thus, such a wavefront may be referred to herein as a "diffractive phase-wrapped wavefront." In some embodiments, the phase-wrapped wavefront may be collapsed at a phase height greater than 1 wave. The decision as to whether a wavefront is collapsed to a phase height greater than 1 wave or to a phase height less than 1 wave may have some practical effects. For example, phase wrapping at greater than 1 wave may reduce diffractive chromatic effects. However, phase wrapping to greater than 1 wave requires more available refractive index change as compared to phase wrapping to less than 1 wave, and any material used is subject to a given range of possible refractive index changes, which may be a limiting factor (e.g., limited by the properties of the material). This may be ultimately overcome in many cases by writing multiple layers or volume filling, however, but there are still limits. So there is a tradeoff between phase wrapping at greater than 1 wave or less than 1 wave. Whether a wave front is phase-wrapped to less than 1 wave or greater than 1 wave may also have implications for energy distribution of far/near vision (e.g., for patients with presbyopia), and the practitioner can control this as necessary to achieve a desired effect.

Figure 5:
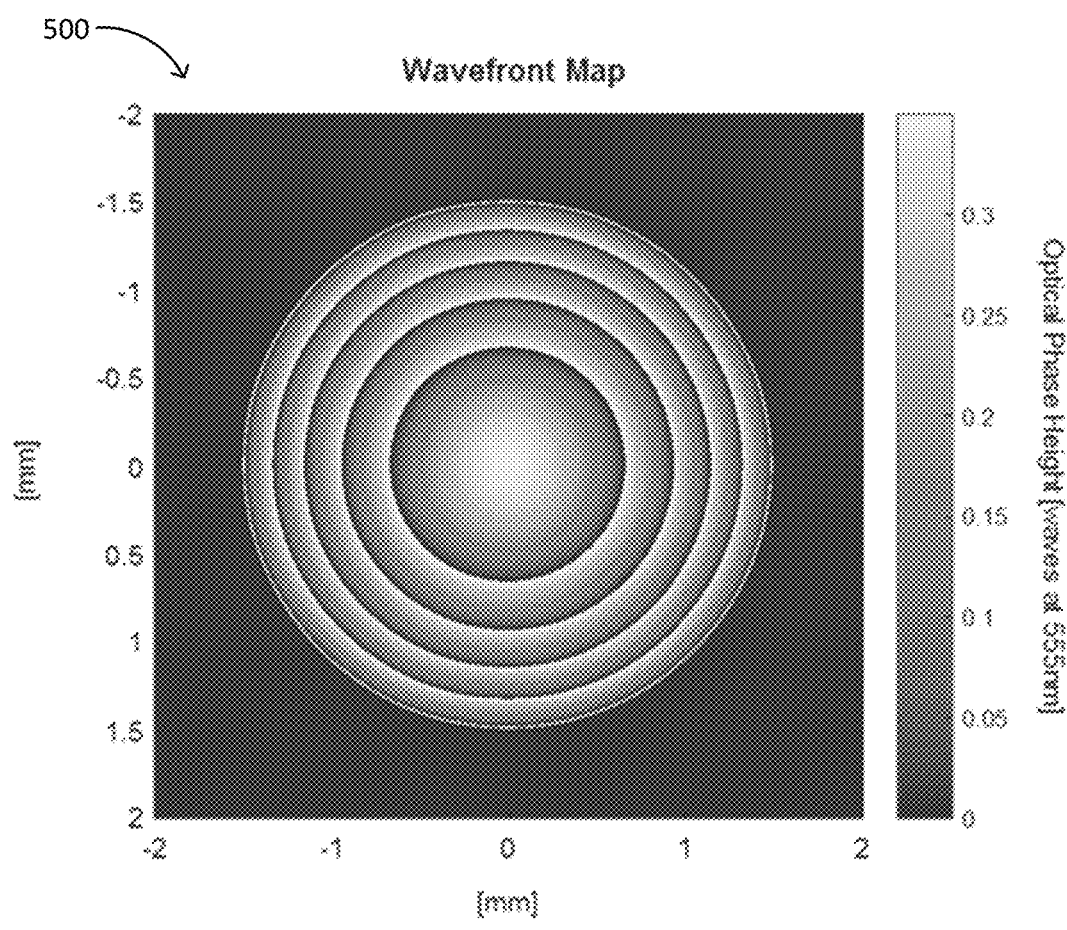
FIG. 5 illustrates a two-dimensional map representation of a phase-wrapped wavefront phase-wrapped at an optical phase height less than 1 wave, such as the wavefront in FIG. 4.

FIG. 5 illustrates a two-dimensional map representation of a phase-wrapped wavefront 500 phase-wrapped at an optical phase height less than 1 wave, such as the wavefront 427 in FIG. 4. The illustrated phase-wrapped wavefront has a 3.0 mm diameter optical zone and a diffractive bifocal with 2.5 Diopters (D) of add-power. The diffractive bifocal wavefront is designed to have an optical phase height of 0.35 waves at 555 nm wavelength. As illustrated, the phase-wrapped wavefront 500 includes five discrete circumferential segments, each segment gradually decreasing in phase height (from 0.35 waves to 0 waves) from an inner boundary of the segment to an outer boundary of the segment.

Figure 6:
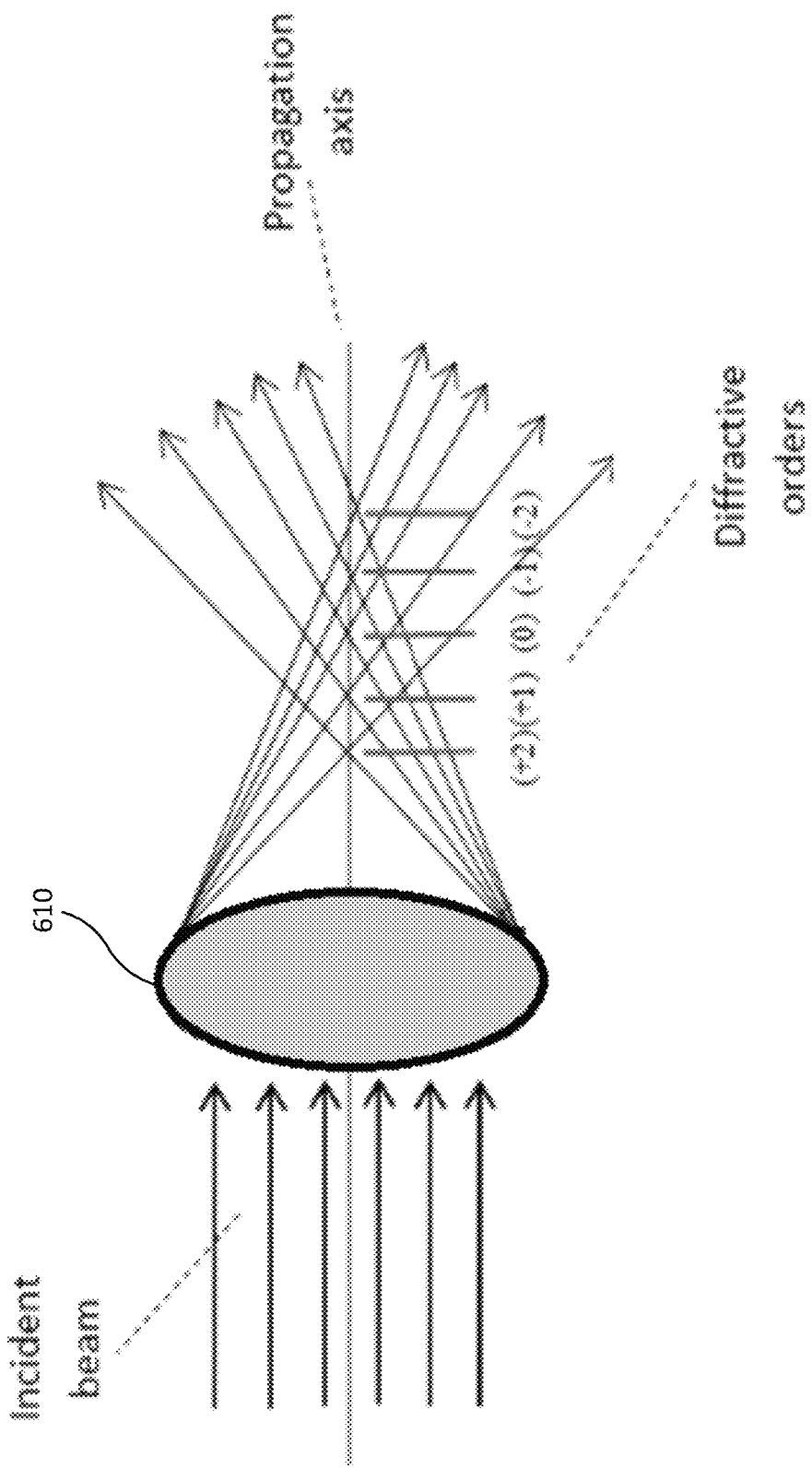
FIG. 6 illustrates an example of an optical structure having diffractive properties.

FIG. 6 illustrates an example of an optical structure 610 having diffractive properties. In some embodiments, an optical structure having a phase-wrapped wavefront collapsed at a phase height other than 1 wave (e.g., less than 1 wave) has diffractive effects that create multiple focal points, which may be useful, for example, in correcting vision in patients having presbyopia. As illustrated in FIG. 6, light rays passing through the optical structure 610, which is an optical structure with diffractive properties, an incident beam can be focused simultaneously at several positions along the propagation axis. Diffraction in this manner can be used to create multiple focal points, for example, to improve the vision of patients with presbyopia. For example, an optical structure having diffractive properties may have a first focal point for near-vision and a second focal point for far-vision.

Figure 7:
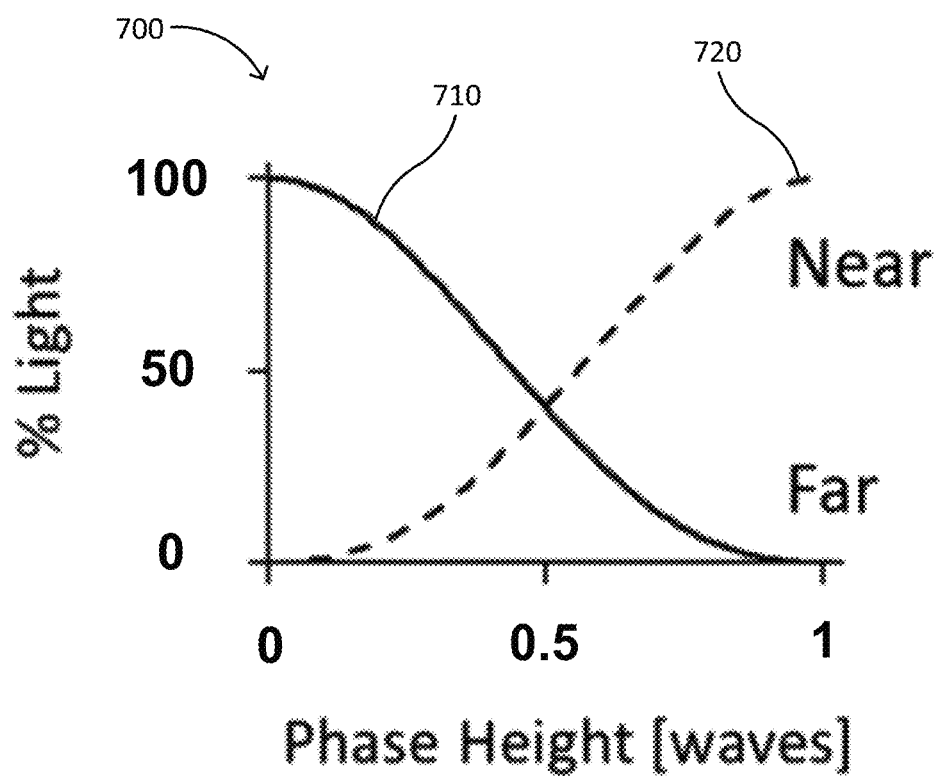
FIG. 7 is a graph illustrating the relative distribution of light between a near-vision focal point and a far-vision focal point as phase height of a wavefront is adjusted between 0 wave and 1 wave.

FIG. 7 is a graph 700 illustrating the relative distribution of light between a near-vision focal point and a far-vision focal point as phase height of a wavefront is adjusted between 0 wave and 1 wave. In some embodiments, the system may generate diffractive phase-wrapped wavefronts (e.g., phase-wrapped wavefronts at less than 1 wave or greater than 1 wave), for conditions such as presbyopia that are designed to provide both high optical quality for far-vision and intermediate- and near-vision (e.g., good through-focus image quality), but with the understanding that there may be a trade-off. An example representation of this trade-off is illustrated in FIG. 7. As illustrated by the far-vision curve 710, as the phase height increases to 1 wave, the percentage of light distributed to the far-vision focal point by the diffraction of incoming light decreases (and therefore image quality for far-vision generally decreases). By contrast, referencing the near-vision curve 720, as the phase height increases to 1 wave, the percentage of light distributed to the near-vision focal point increases (and therefore image quality for near-vision generally increases). In some embodiments, a desired distribution for this tradeoff may be specified in an optical prescription (e.g., as add power), and may be determined based on any suitable of patient-dependent factors. For example, the patient who often engages in high-detail work (e.g., a watchmaker) may require a relatively high add power (e.g., 4.0 diopters). A relatively low add power (e.g., 1.0 diopters) may be suitable for a patient who does not engage in such high-detail work. A diffractive phase-wrapped wavefront may be generated with a prescription having such considerations in mind to come to a desired trade-off.

In some embodiments, the one or more processors may be configured to generate multiple wavefronts, for example, to correct multiple aberrations of the eye. In some embodiments, the one or more processors may generate a second variable wavefront based on a second optical prescription, wherein the second optical prescription comprises an add power for multifocal vision correction. The term second optical prescription does not necessarily reference a separate prescription, and may instead refer to separate one or more parameters for correcting a different aberration than the first optical prescription. For example, a patient may receive a single prescription from an optometrist for correcting near-vision based on parameters of a first optical prescription and for correcting far-vision based on parameters of a second optical prescription (e.g., including an add power). In some embodiments, the one or processors may phase-wrap the second variable wavefront, wherein phase wrapping the second variable wavefront comprises collapsing the second variable wavefront to a second phase-wrapped wavefront having a second predetermined phase height. The second predetermined phase height may be less than 1 wave, so as to allow for diffractive effects as discussed above. In some embodiments, a first phase-wrapped wavefront may have a phase height of 1 wave, and the second phase-wrapped wavefront may have phase height less than 1 wave. In these embodiments, the first phase-wrapped wavefront may be useful for correcting myopia and the second phase-wrapped wavefront may be useful for correcting presbyopia, for example.

Figure 8:
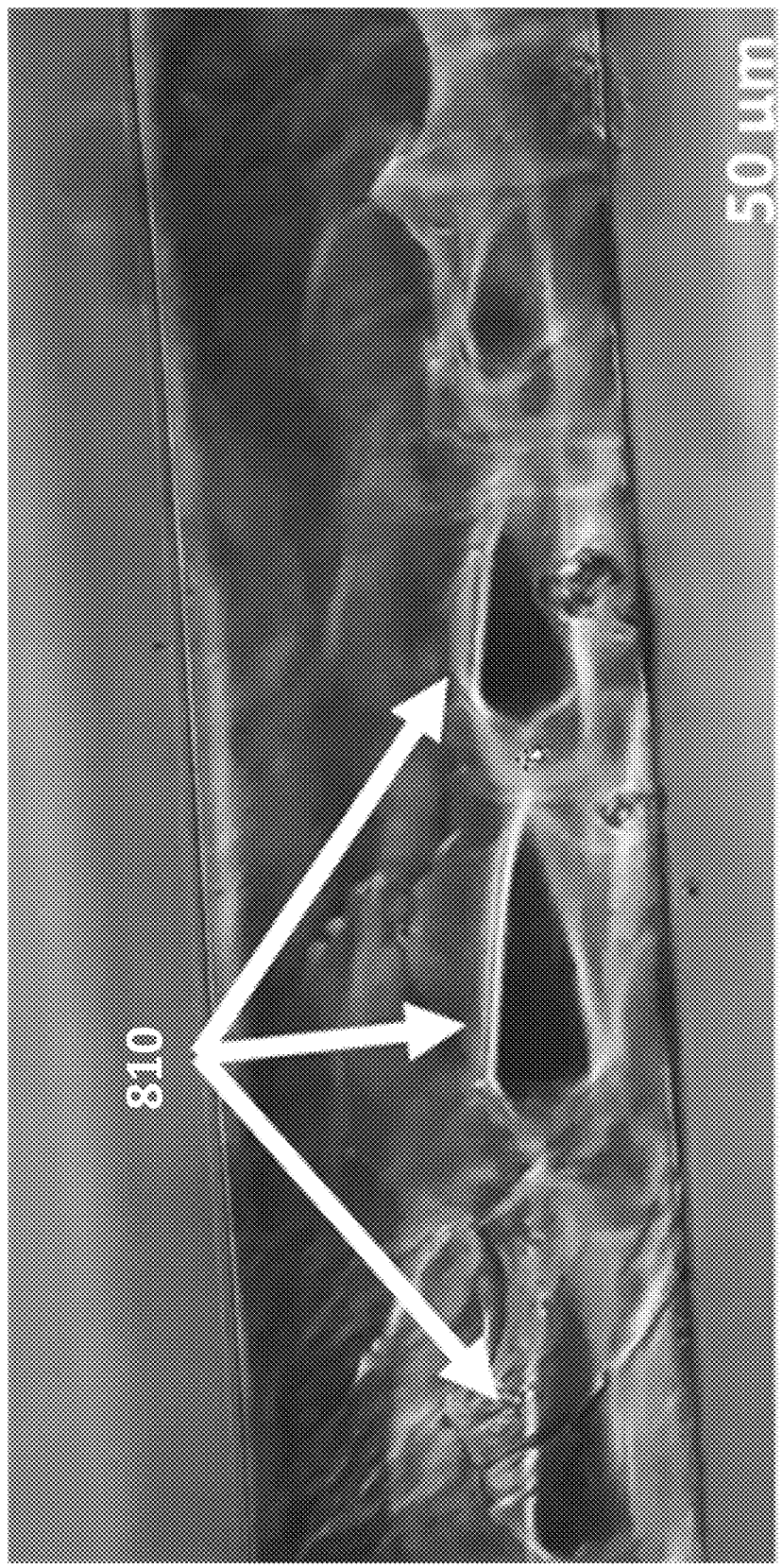
FIG. 8 illustrates a cross section of an ophthalmic lens including a subsurface optical structure having multiple substructures.

FIG. 8 illustrates a cross section of an ophthalmic lens including a subsurface optical structure having multiple substructures 810. In some embodiments, the one or more processors may be configured to generate, based on the first phase-wrapped wavefront, energy output parameters for forming a first optical structure using an energy source. In some embodiments, the first optical structure may be configured to refract light directed at the retina of the patient so as to improve vision. In some embodiments, the optical structure may be a subsurface optical structure. For example, referencing the cross-section illustrated in FIG. 8, the optical structure may be a subsurface optical structure having multiple substructures 810 that may be concentric. As discussed in further detail above, subsurface optical structures may be achieved by focusing laser pulses appropriately to depths within the ophthalmic lens such that changes in refractive property occur to sub-volumes in the interior of the ophthalmic lens.

The conventional approach for forming a diffractive ophthalmic lens involves creating Fresnel rings that project outward from an exterior surface of the ophthalmic lens. Such a configuration not only increases the thickness profile of the lens, but it may also cause issues with the optical properties of the ophthalmic lens. For example, in the case of a contact lens, disposing Fresnel rings on the outward-facing exterior surface of the contact lens may cause errors in light diffraction or refraction because the level of tear film may vary across the peaks and valleys of the Fresnel rings. And disposing the Fresnel rings on the inward-facing exterior surface of the contact lens may cause patient discomfort. Additionally, rings disposed on an exterior surface of the ophthalmic lens may become sites for the accumulation of debris which causes light scatter and loss of contrast.

Moreover, conventional approaches rely on changes in the thickness of ophthalmic lenses to supply the base power of the ophthalmic lenses. In these approaches, the refractive index of the material throughout an ophthalmic lens may remain constant. This reliance on thickness necessarily means that lenses with relatively high base powers are relatively thick. For contact lenses, this may mean patient discomfort. For IOLs, this may mean an increase in patient risk during surgery, and a higher potential for complications (e.g., because it may be more difficult to get the IOL seated in the capsular bag). By contrast, the disclosed methods of creating subsurface optical structures using an energy system (e.g., a laser) does not rely on changing the thickness of an ophthalmic lens for the base power. Rather, as explained above, refractive indices of subvolumes within the ophthalmic lens are modified to supply the base power of the ophthalmic lens and thereby refract and/or diffract light as desired. Finally the use of an energy system as described below with respect to optical zones provides increased resolution as compared to more conventional techniques such as cryolathes or molded injection.

Figure 9A:
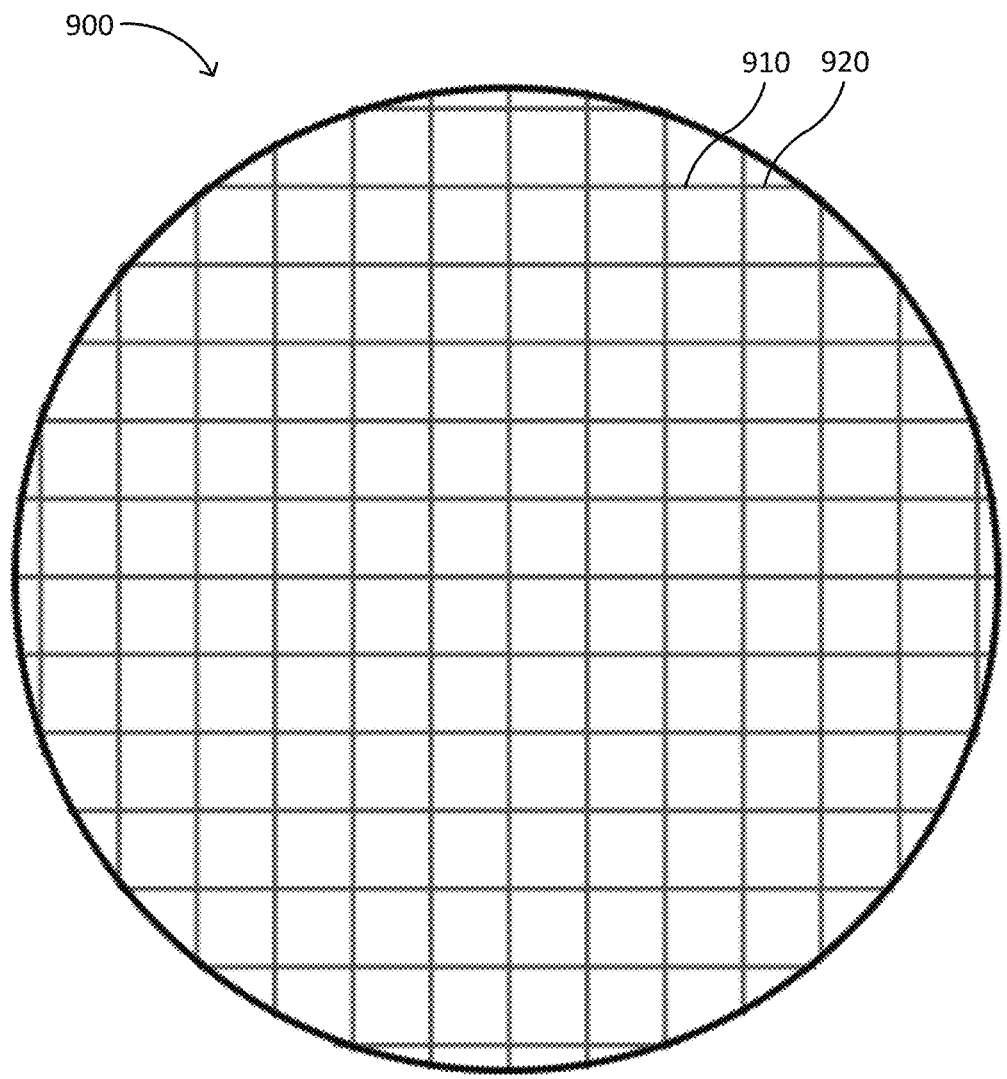
FIGS. 9A-9B illustrate example conceptualizations of an ophthalmic lens having a plurality of optical zones.
Figure 9B:
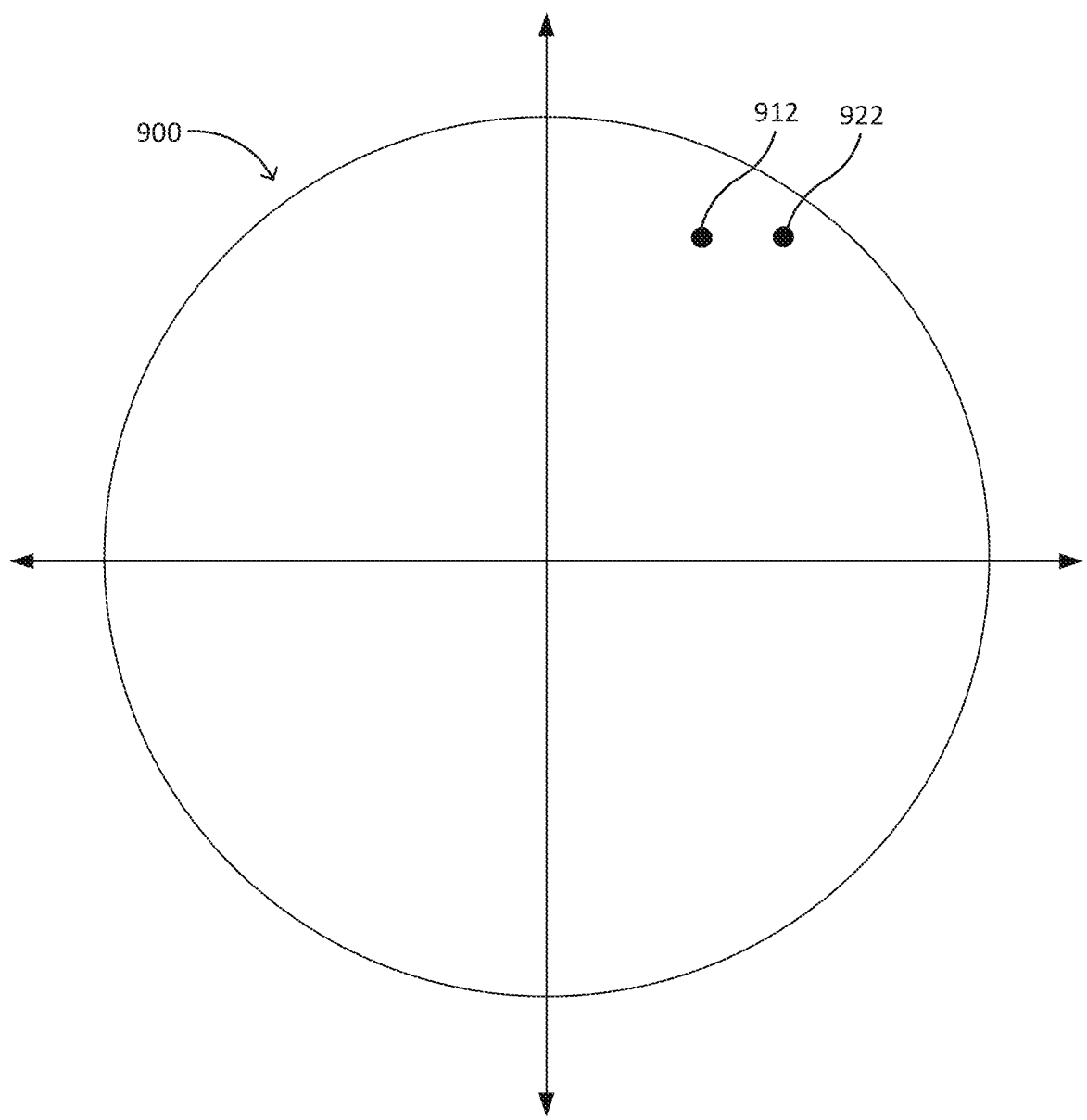

FIGS. 9A-9B illustrate example conceptualizations of an ophthalmic lens 900 having a plurality of optical zones. In some embodiments, an ophthalmic lens may be divided up into a plurality of pixels, each pixel corresponding to an optical zone. An optical zone may be a sub-region or a sub-volume of an ophthalmic lens. This is illustrated in FIG. 9A, which shows the ophthalmic lens 900 divided up into a plurality of pixels (e.g., the pixels 910 and 920) in a grid fashion. Although FIG. 9A illustrates uniform pixels that are square shaped, this disclosure contemplates that pixels may be of any suitable shape (e.g., hexagonal, pentagonal, circular) and that they may not be uniform (e.g., they may be of different shapes and sizes). A pixel area may correspond to the resolution of an energy delivery system (e.g., a laser system) configured to form an optical structure corresponding to a phase-wrapped wavefront. That is, a pixel area may correspond to a minimum area of a sub-region of the ophthalmic lens at which the energy delivery system may focus an energy beam (e.g., a laser pulse) to change a refractive index of the sub-volume associated with the sub-region. FIG. 9B illustrates another conceptualization of optical zones, where the ophthalmic lens is not divided up into discrete pixels. Instead, the ophthalmic lens is mapped out using a coordinate system (e.g., a two-dimensional x-y coordinate system, a three-dimensional x-y-z coordinate system, or a polar coordinate system (radius and angle)). For example, the points 912 and 922 may each have a respective coordinate in the coordinate system.

In some embodiments, the generated energy output parameters may specify an amount of power that is to be delivered by the energy delivery system at one or more optical zones. For example, referencing FIG. 9A, the energy output parameters may specify power levels (e.g., in Watts) for one or more laser pulses that are to be delivered by a laser system at the pixel 910 and the pixel 920. Similarly, referencing FIG. 9B, the energy output parameters may specify power levels for a plurality of coordinates associated with the ophthalmic lens (e.g., the points 912 and 922). In some embodiments, the generated energy output parameters may specify a duration during which energy beam may be directed at one or more optical zones. For example, the energy output parameters may specify pulse durations for directing a laser beam at one or more of the optical zones. In some embodiments, the energy output parameters may specify a depth at which energy beam is to be delivered in forming an optical structure. For example, the energy output parameters may specify that a first set of pulses is to be delivered to a set of optical zones at a first depth along a first layer of the ophthalmic lens, and may further specify that a second set of pulses is to be delivered to a second set of optical zones at a second depth along a second layer of the ophthalmic lens. In this example, the first layer may be based on a phase-wrapped wavefront collapsed at 1 wave (e.g., for correcting myopia), and the second layer may be based on a phase-wrapped wavefront collapsed at less than 1 wave (e.g., for correcting presbyopia). The first set of pulses in this example may be associated with a first set of energy output parameters (e.g., power levels, pulse durations, depths) for a plurality of optical zones, and the second set of pulses in this example may be associated with a second set of energy output parameters.

In some embodiments, the one or more processors, and generating the energy output parameters, may apply a calibration function so as to create a tailored set of parameters for real-world conditions. The calibration function may depend on any suitable factors. For example, the one or more processors may apply a calibration function based on one or more of a material property of the ophthalmic lens, a gender of the patient, an age of the patient, a depth at which an optical structure (e.g., a subsurface optical structure) is to be formed in the ophthalmic lens, a number of layers, the distance by which different layers are separated, and/or properties of an energy source for which the energy output parameters are generated (e.g., scan speed, numerical aperture, wavelength, pulse width, repetition rate, writing depth, line-spacing, scan architecture).

In some embodiments, the one or more processors may be configured to generate energy output parameters for forming multiple optical structures. For example, the one or more processors may generate energy output parameters for forming a first subsurface optical structure based on a first phase-wrapped wavefront having a phase height of 1 wave (e.g., for correcting myopia) and a second subsurface optical structure based on a second phase-wrapped wavefront having a phase height less than 1 wave so as to diffract light (e.g., for correcting presbyopia). In these embodiments, what results may be a multifocal ophthalmic lens configured to create multiple focal points within the eye. In some embodiments, these optical structures may be formed as distinct layers (e.g., in a cornea, a contact lens, an intraocular lens). In other embodiments, the one or more processors may generate parameters for forming a single optical structure as a single layer that combines the first phase-wrapped wavefront and the second phase-wrapped wavefront such that the single layer has the effects specified by the two wavefronts.

In some embodiments, the system may further include an energy source configured to direct one or more energy beams toward the optical structure so as to form the first optical structure based on the energy output parameters. In other embodiments, the system may not include such an energy source, and may simply send the energy output parameters to a different system that includes an energy source for forming optical structures. In some embodiments, the energy source may be a laser source configured to deliver targeted pulsed or continuous-wave laser beams.

Although the examples in the disclosure focus on correction of standard sphere/cylinder error and/or presbyopia, the disclosure contemplates the generation of wavefronts that may be used to form optical structures for correcting any suitable aberration (e.g., customized higher order aberrations, myopia progression peripheral error). For example, wavefronts described by any combination of Zernike polynomials may be generated. Although the disclosure focus is on subsurface optical structures, disclosure contemplates any suitable optical structures, for example, optical structures that are not subsurface.

Figure 10:
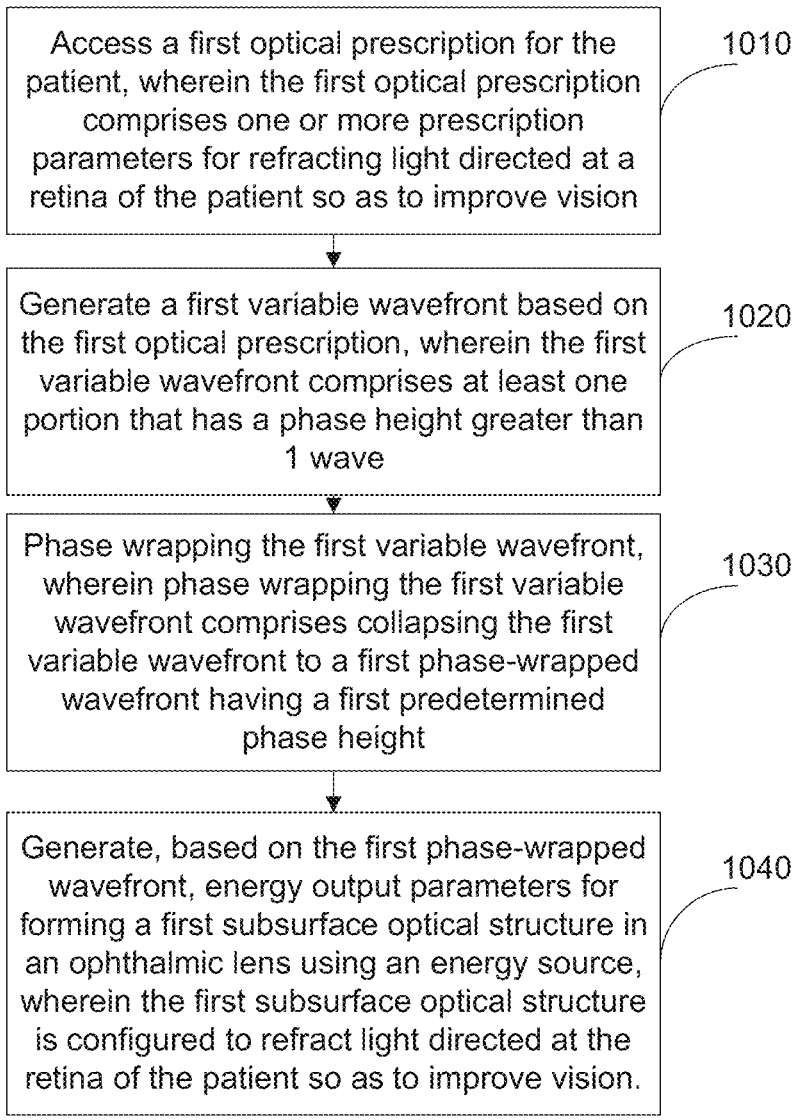
FIG. 10 illustrates an example method for determining parameters for forming a subsurface optical structure for improving vision in a patient.

FIG. 10 illustrates an example method 1000 for determining parameters for forming a subsurface optical structure for improving vision in a patient. The method may include, at step 1010, accessing a first optical prescription for the patient, wherein the first optical prescription comprises one or more prescription parameters for refracting light directed at a retina of the patient so as to improve vision. At step 1020, the method may include generating a first variable wavefront based on the first optical prescription, wherein the first variable wavefront comprises at least one portion that has a phase height greater than 1 wave. At step 1030, the method may include phase wrapping the first variable wavefront, wherein phase wrapping the first variable wavefront comprises collapsing the first variable wavefront to a first phase-wrapped wavefront having a first predetermined phase height. At step 1040, the method may include generating, based on the first phase-wrapped wavefront, energy output parameters for forming a first subsurface optical structure in an ophthalmic lens using an energy source, wherein the first subsurface optical structure is configured to refract light directed at the retina of the patient so as to improve vision.

Particular embodiments may repeat one or more steps of the method of FIG. 10, where appropriate. Although this disclosure describes and illustrates particular steps of the method of FIG. 10 as occurring in a particular order, this disclosure contemplates any suitable steps of the method of FIG. 10 occurring in any suitable order. Moreover, although this disclosure describes and illustrates an example method for determining parameters for forming a subsurface optical structure for improving vision in a patient, including the particular steps of the method of FIG. 10, this disclosure contemplates any suitable method for determining parameters for forming a subsurface optical structure for improving vision in a patient, including any suitable steps, which may include all, some, or none of the steps of the method of FIG. 10, where appropriate. Furthermore, although this disclosure describes and illustrates particular components, devices, or systems carrying out particular steps of the method of FIG. 10, this disclosure contemplates any suitable combination of any suitable components, devices, or systems carrying out any suitable steps of the method of FIG. 10.

Figures 11, 12:
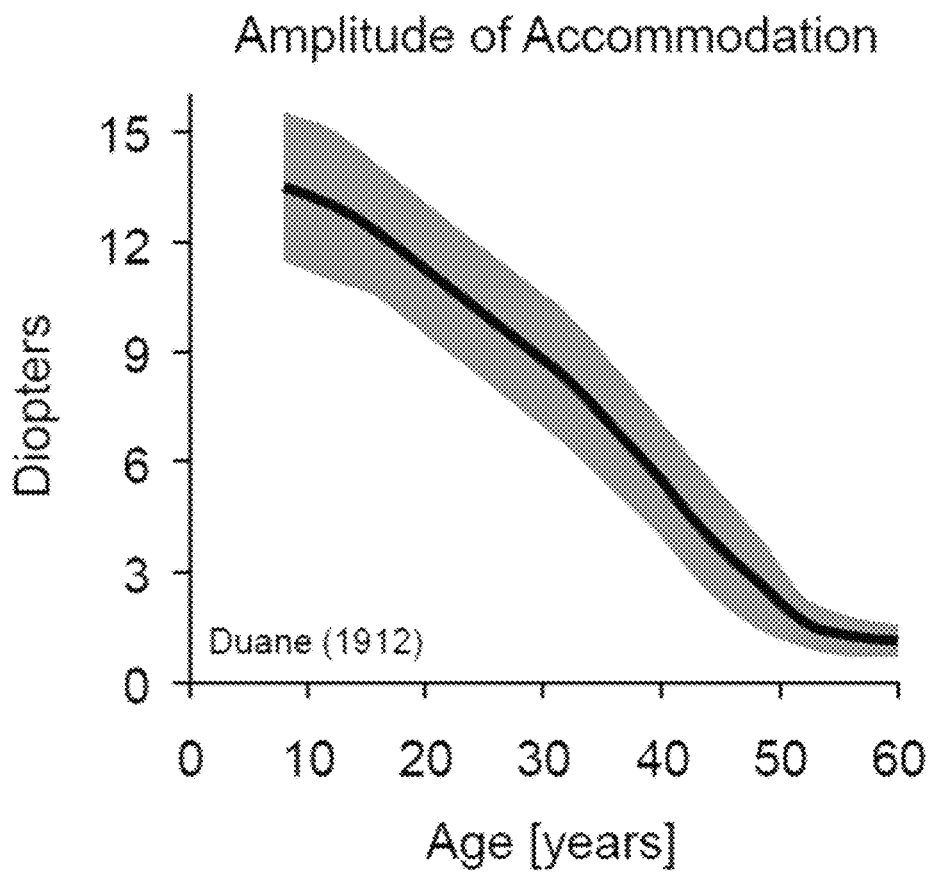
FIG. 11 illustrates an example of presbyopia progression in a patient.
FIG. 12 illustrates an example chart of presbyopia progression.

FIG. 11 illustrates an example of presbyopia progression in a patient. In order to focus on objects near to the eye, the natural lens of the eye (e.g., the human crystalline lens) needs to be able to accommodate, or change its shape to appropriately focus the convergence of light rays on the retina from the object. This is accomplished by contraction of the ciliary muscles coupled to the lens. As a patient ages, the natural lens tends to stiffen (a reduction in elasticity) and/or grow in size (axial and/or equatorial growth) with age, making it increasingly difficult for the ciliary muscle to cause the lens to accommodate appropriately. As a result, the patient may experience a reduction in the ability to focus on near or intermediate objects. This condition may be termed presbyopia, and an example progression is illustrated in FIG. 11, which shows the amplitude of accommodation possible with a patient's natural lens as a function of age. A diopter may be defined as 1/d, where d is an distance between the eye and an object in meters. As illustrated, the patient may have a relatively high amplitude of accommodation at age 10, being able to appropriately accommodate for objects as near as around $\frac{1}{13}$ or $\frac{1}{14}$ meters away from the eye (i.e., 13 or 14 diopters). As the patient ages, this amplitude of accommodation gradually begins to decrease. At around the age of 40, presbyopia typically begins to be noticeable. In the example of FIG. 11, at around the age of 40, the patient may be unable to appropriately accommodate for objects farther than $\frac{1}{4}$ meters away. Generally, patients less than 45 years old may be classified as early presbyopes requiring relatively minor correction. Presbyopia patients between 45 and 55 years old may be classified as mid presbyopes requiring a moderate level of correction. Referencing FIG. 11, the presbyopia in the patient during this age range may have progressed such that the patient is unable to appropriately accommodate for objects farther than $\frac{1}{2}$ meters away. Presbyopia patients over the age of 55 years old (or patients who have received a non-accommodating intraocular lens) may be classified as advanced presbyopes requiring a relatively large level of correction. Referencing FIG. 11, the presbyopia in the patient after 55 years may have progressed such that the patient can no longer accommodate for objects closer than 1 meter away.

FIG. 12 illustrates an example chart of presbyopia progression. FIG. 12 shows typical accommodating ability for early presbyopes, mid presbyopes, and advanced presbyopes (or those with a monofocal non-accommodating IOL). FIG. 12 also shows appropriate add powers that may be needed to improve near and/or intermediate vision for each respective stage of presbyopia progression. For example, an early presbyope may need 1 diopter of add power, a mid presbyope may need 2 diopters of add power, and an advanced presbyope may need 3 diopters of add power. These add powers may be provided by, for example, providing optical structures (e.g., subsurface optical structures within an ophthalmic lens) that implement an appropriate wavefront capable of diffracting light so as to refocus light rays coming from an object.

Figure 13:
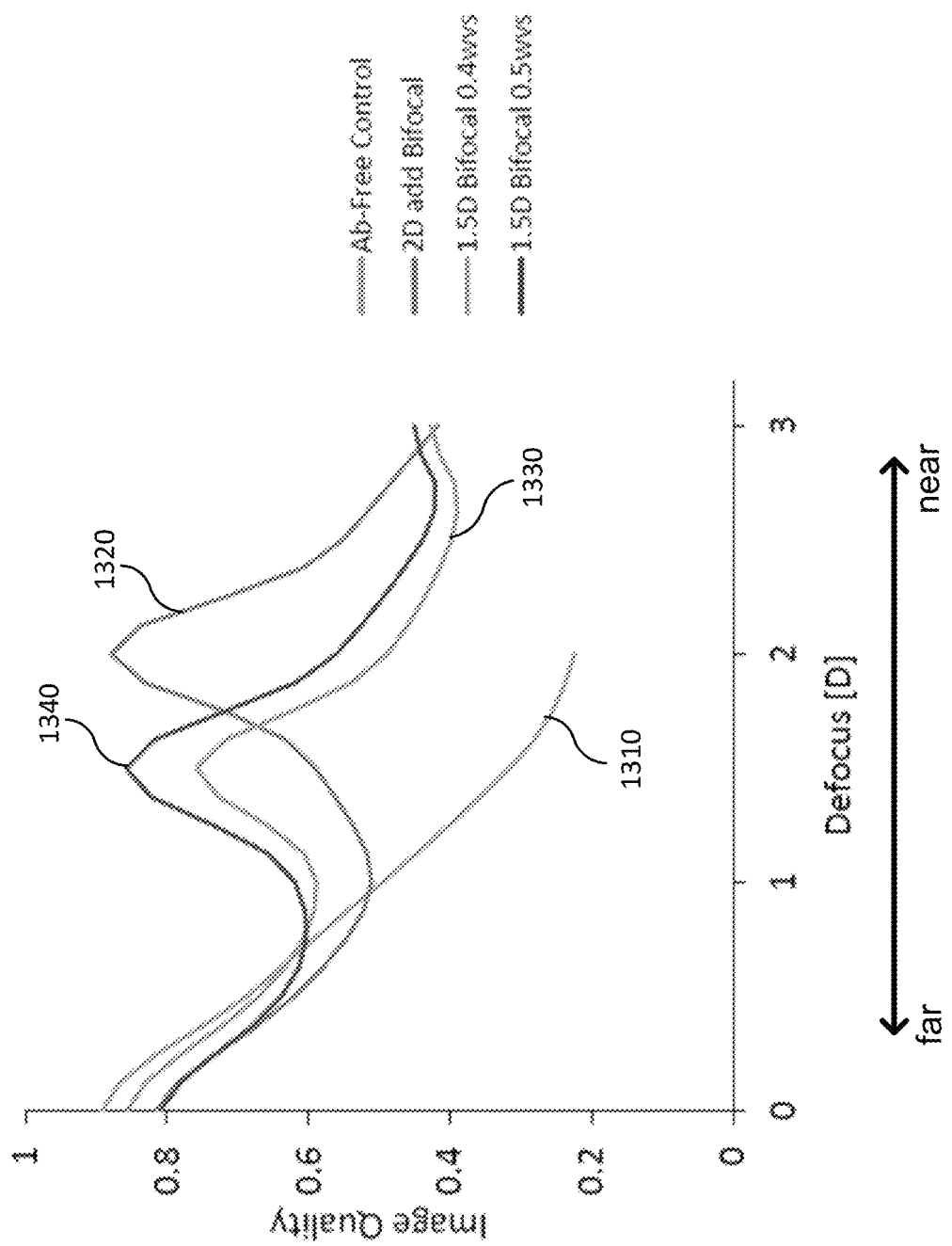
FIG. 13 illustrates example image quality metrics across a diopter range using a number of bifocal wavefronts.

FIG. 13 illustrates example image quality metrics across a diopter range using a number of bifocal wavefronts.

Referencing FIG. 13, the line 1310 illustrates an example of image quality as a function of defocus (in units of diopters) for a patient with presbyopia. The patient has relatively high image quality at low diopters corresponding to far vision (e.g., an image-quality value of around 0.9 at 0 diopters where an object is infinitely far away) and relatively low image quality at high diopters corresponding to near vision (e.g., an image-quality value of around 0.2 at 2 diopters where an object is 0.5 meters away). The image quality metrics shown in FIG. 13 (and similarly in FIGS. 15, 16, 17, and 18) are known as the "image convolution metric," which numerous studies have shown to be an excellent proxy for high contrast visual acuity. More information about such metrics may be found in the following references, which are incorporated herein in their entirety for all purposes: Watson, Andrew B. et al., "Predicting visual acuity from wavefront aberrations." *Journal of Vision* 8.4 (2008): 17-17; Zheleznyak, Len et al., "Modified monovision with spherical aberration to improve presbyopia through-focus visual performance," *Investigative Ophthalmology & Visual Science* 54.5 (2013): 3157-3165; Zheleznyak, Len et al., "Impact of pupil transmission apodization on presbyopia through-focus visual performance with spherical aberration," *Investigative Ophthalmology & Visual Science* 55.1 (2014): 70-77; and Kim, Myoung Joon, et al., "Improving Through-Focus Visual Performance Using Primary And Secondary Spherical Aberrations," *Investigative Ophthalmology & Visual Science* 53.14 (2012): 6332-6332.

The typical way of improving near vision in patients with presbyopia is causing light to diffract to multiple focal points using an optical element. For example, a bifocal contact lens, a bifocal IOL, or a cornea modification may be used to focus light rays from objects at two focal points—e.g., a first focal point for nearby objects and a second focal point for far objects. Referencing FIG. 13, the line 1320 corresponds to a conventional bifocal lens with a 2-diopter add power. As illustrated, the bifocal lens diffract slate so as to create two peaks of high image quality—the first peak at 0 diopters and the second peak at around 2 diopters—corresponding to the two focal points of the bifocal. This typically results in an overall improvement of vision by allowing the patient to see relatively well around the two peaks, but it is nonetheless suboptimal because there is a large range in between the peaks (intermediate vision) where image quality drops off significantly.

In some embodiments, the range in between the peaks can be shortened using an ophthalmic lens with a lower diopter value. For example, a 1.5-diopter bifocal may be used instead of a 2-diopter bifocal. Doing so shifts the image-quality peak toward better intermediate vision as compared to an ophthalmic lens with a higher diopter value, but reduces image quality for a range of near vision. In some embodiments, the ophthalmic lens may be made to correspond to a wavefront generated using the phase-wrapping process described previously. That is, the wavefront of a typical bifocal may be collapsed to a predetermined phase height that is less than 1 wave. For example, referencing FIG. 13, the lines 1330 and 1340 correspond to 1.5-diopter bifocal with a wavefront that has been collapsed to 0.4 waves and 0.5 waves respectively. As illustrated, phase-wrapping the wavefront adjusts the curvature of the image-quality line. An optimal phase height and an optimal add power of the lens may be determined based on the "visual diet" of the patient, e.g., which may correspond to the relative percentages of time the patient focuses at each distance on an average day. As is evident from these lines, implementing diffractive wavefronts generally involves significant trade-offs among near, intermediate, and far vision. That is, these diffractive wavefronts on their own are typically unable to create optimal vision across the entire range of a patient's vision from near vision to far vision. For example, while the lines 1330 and 1340 corresponding to the phase-wrapped wavefronts may be an improvement over the line 1320 corresponding to the conventional bifocal, they still have an intermediate-vision range in between their respective peaks that provides suboptimal image quality.

Figure 14:
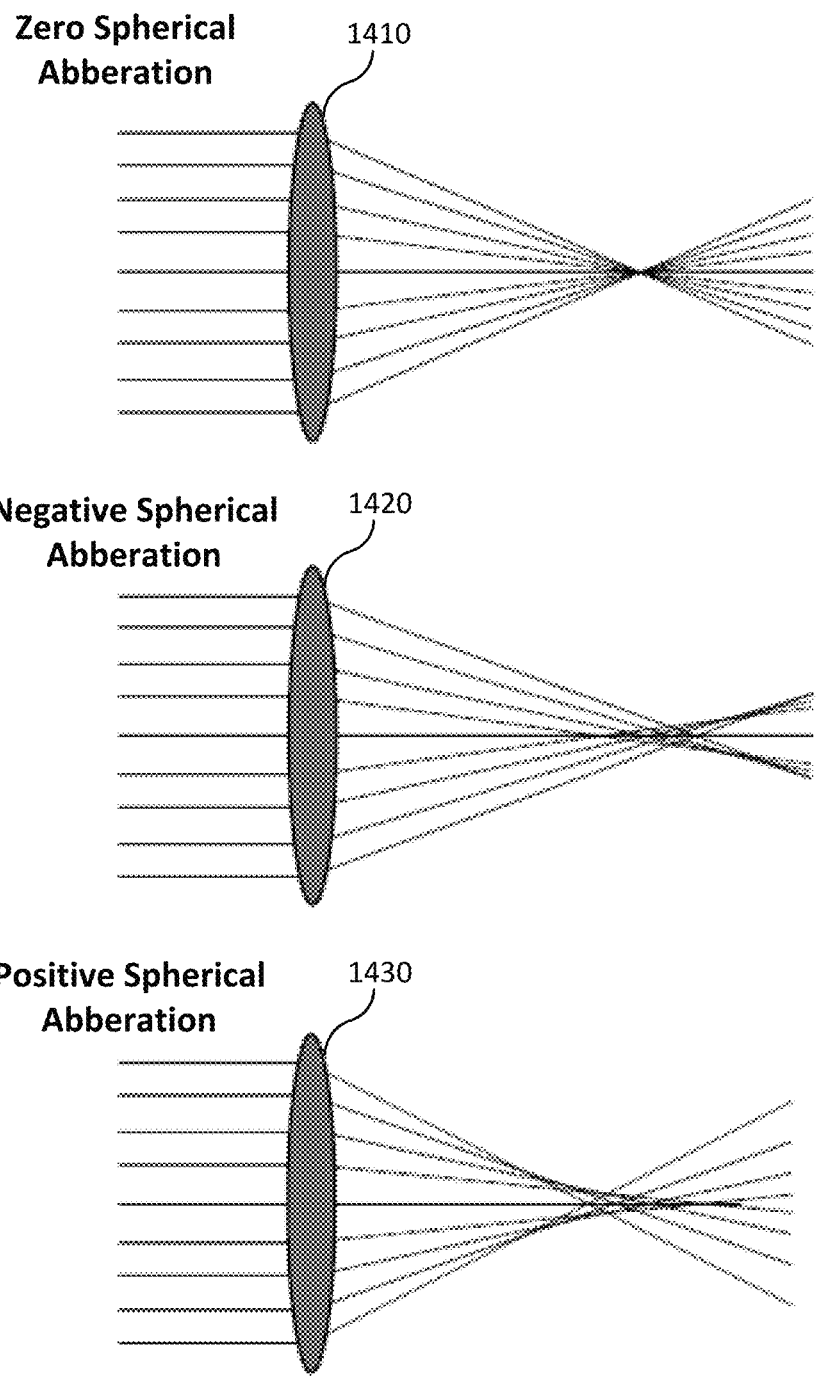
FIG. 14 illustrates the concept of spherical aberrations in lenses.

FIG. 14 illustrates the concept of spherical aberrations in lenses. Typically, all spherical lenses have some degree of spherical aberration. As illustrated in FIG. 14, a lens 1410 with zero spherical aberration focuses all incoming rays of light at a single focal point. In some embodiments, an ophthalmic lens may be made to deliberately introduce a spherical aberration in order to refocus light to help correct presbyopia. There may be two general types of spherical aberrations: negative spherical aberrations and positive spherical aberrations. Negative spherical aberrations cause peripheral rays (rays closer to the periphery of the lens 1420) passing through the lens 1420 to be refracted by a smaller amount than central rays (rays closer to the center, or optical axis, of the lens 1420). Thus, as illustrated in FIG. 14, the more central rays passing through the lens 1420 come to a focal point prior to the more peripheral rays. Positive spherical aberrations cause the peripheral rays passing through the lens 1430 to be refracted by a larger amount than the central rays. Thus, as illustrated in FIG. 14, the more peripheral rays passing through the lens 1430 come to a focal point prior to the more central rays.

Figure 15:
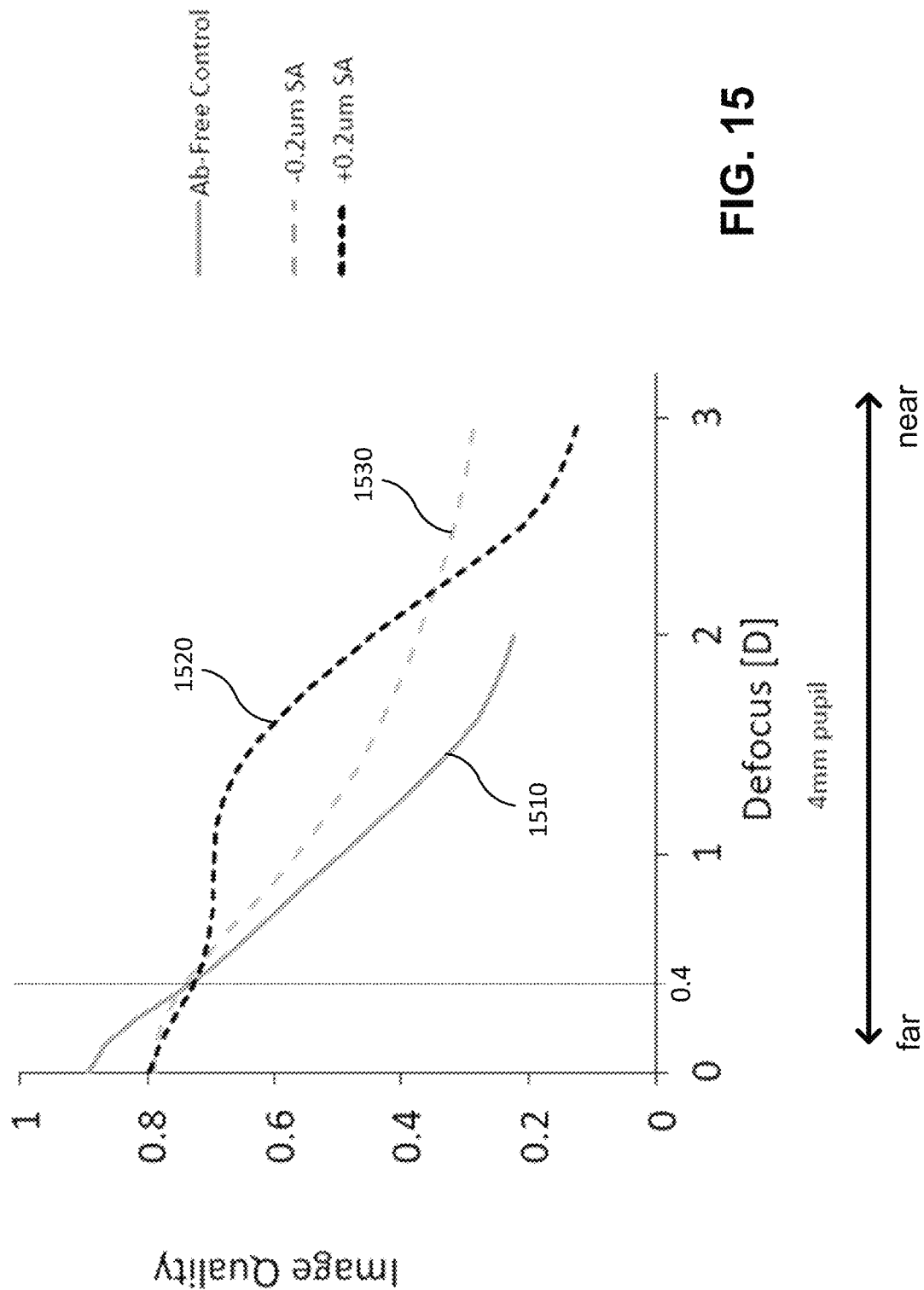
FIG. 15 illustrates example image quality metrics for a patient with presbyopia with lenses having positive and negative spherical aberrations as compared to a control with zero spherical aberration.

FIG. 15 illustrates example image quality metrics for a patient with presbyopia with lenses having positive and negative spherical aberrations as compared to a control with zero spherical aberration. Introducing spherical aberrations (both positive and negative) may generally decrease image quality for far vision as compared to the control, but may increase image quality for near and intermediate vision. For example, referencing FIG. 15, the lines 1520 and 1530 corresponding to positive and negative spherical aberrations, respectively, produce a decrease in image quality at the extreme of far vision (e.g., at 0 diopters) as compared to the control 1510, and an increase in image quality at more intermediate and near ranges (e.g., after about 0.4 diopters) as compared to the control 1510. As is evident from FIG. 15, positive and negative spherical aberrations have their own trade-offs (e.g., with positive spherical aberrations as illustrated by the line 1520 producing better intermediate vision but worse near vision than negative spherical aberrations as illustrated by the line 1530). As FIG. 15 illustrates, although spherical aberrations can be used to provide an improvement over a control with zero aberrations, they are overall limited in their capability for providing an extended range of high image quality from near to far vision. That is, while they provide some gains in far vision, there is a drop-off when it comes to near and/or intermediate vision.

Figure 16:
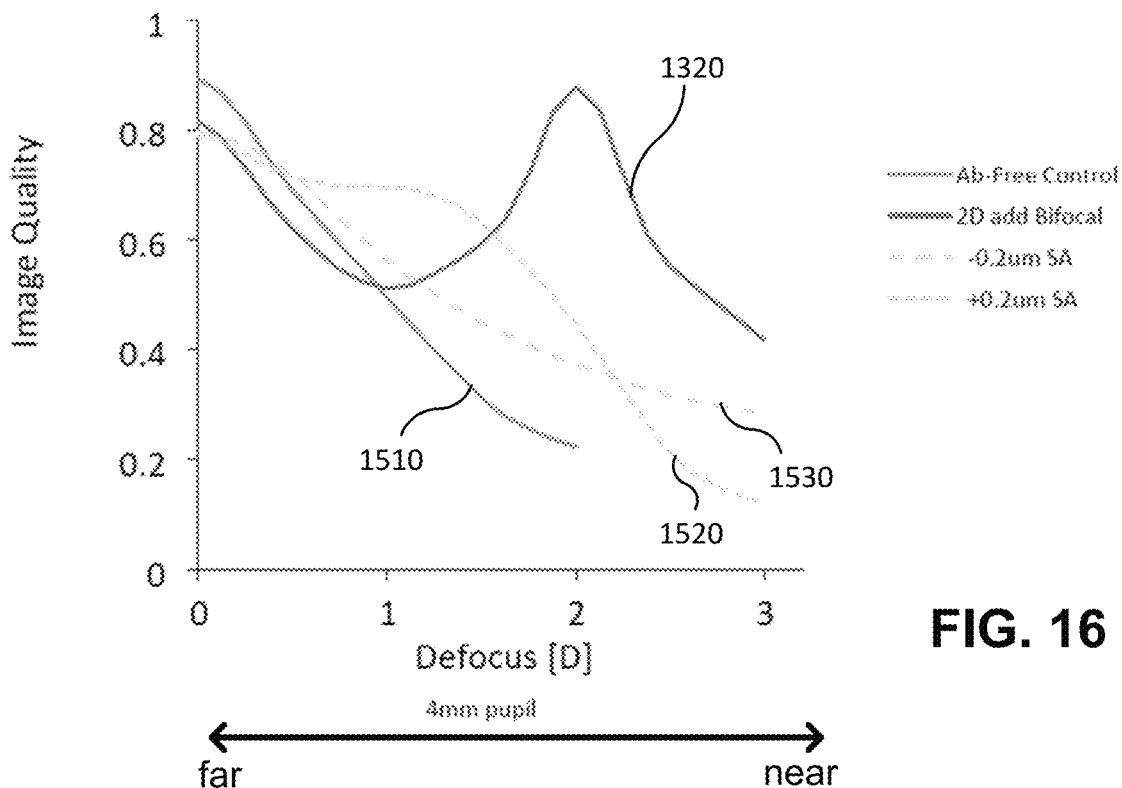
FIG. 16 illustrates a graph overlaying the line for a 2-diopter bifocal of FIG. 13 with the spherical aberration lines, and the control line of FIG. 15.

FIG. 16 illustrates a graph overlaying the line 1320 for a 2-diopter bifocal of FIG. 13 with the spherical aberration lines 1520, 1530 and the control line 1510 of FIG. 15. As can be seen in the example of FIG. 16, the image quality metrics of the bifocal line 1320 (e.g., at and around the 2-diopter peak) provide an improvement to the drop-off in near and/or intermediate vision that occurs on the spherical aberration lines 1520, 1530. And the image quality metrics of the spherical aberration lines 1520, 1530 provide an improvement to the valley between the peaks of the bifocal line 1320 (e.g., between about zero and 2 diopters). Thus, there are qualities for both spherical aberrations and multifocals (e.g., bifocals) that may be complementary to each other. Embodiments of the disclosure attempt to create a lens corresponding to a unified wavefront that merges both qualities together, as will be explained below.

Figure 17:
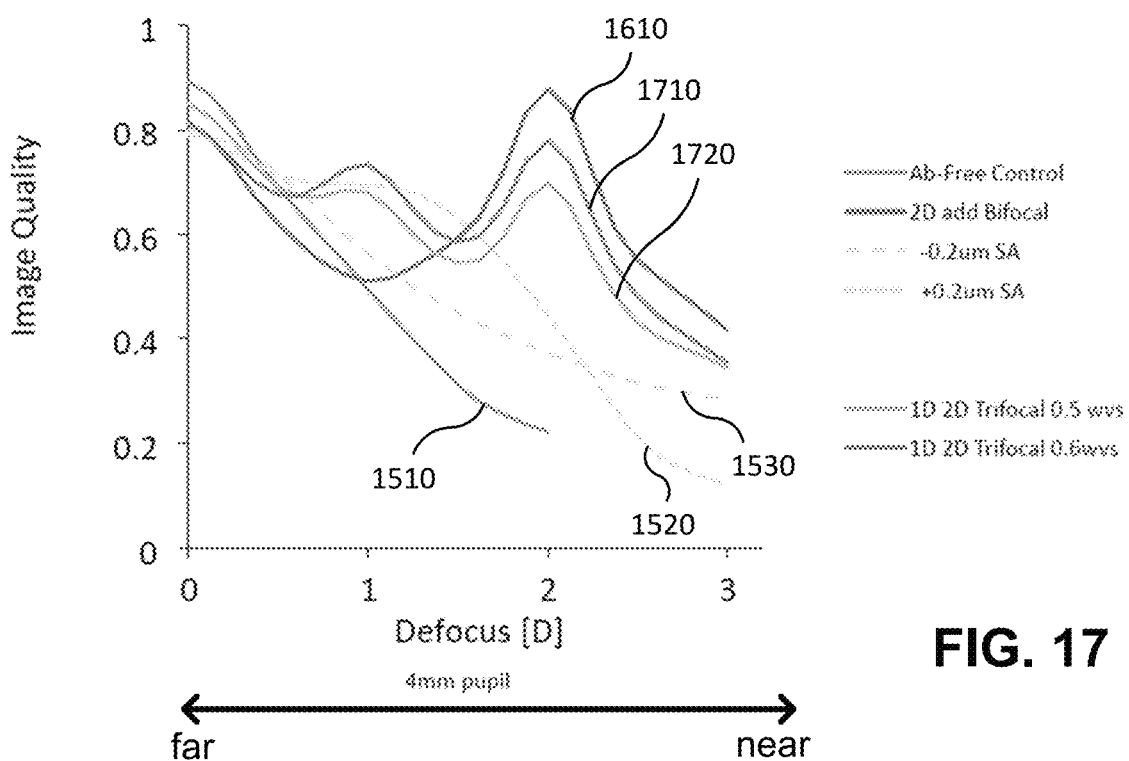
FIG. 17 illustrates the graph of FIG. 16 further overlaying lines corresponding to image quality metrics of phase-wrapped trifocals.

FIG. 17 illustrates the graph of FIG. 16 further overlaying lines corresponding to image quality metrics of phase-wrapped trifocals. The lines 1710 and 1720 both correspond to trifocals centered at 1 diopter and 2 diopters, but the line 1710 corresponds to a trifocal phase wrapped at 0.6 waves and the line 1720 corresponds to a trifocal phase wrapped at 0.5 waves. As illustrated, the trifocals provide an improvement over the bifocal corresponding to the line 1610 over the range between 0 and 2 diopters. For example, the trifocals provide an additional peak at 1 diopter and generally reduce drop-offs in image quality between their peaks (i.e., in the illustrated example, between the peaks at 0 and 1 diopter and between the peaks at 1 and 2 diopters) due to their respective phase wrapping. However, the drop-offs between peaks may not allow for consistent image quality, which may be perceptible to the patient, and as such may still not be ideal in providing a seamless extended range of vision.

Figure 18:
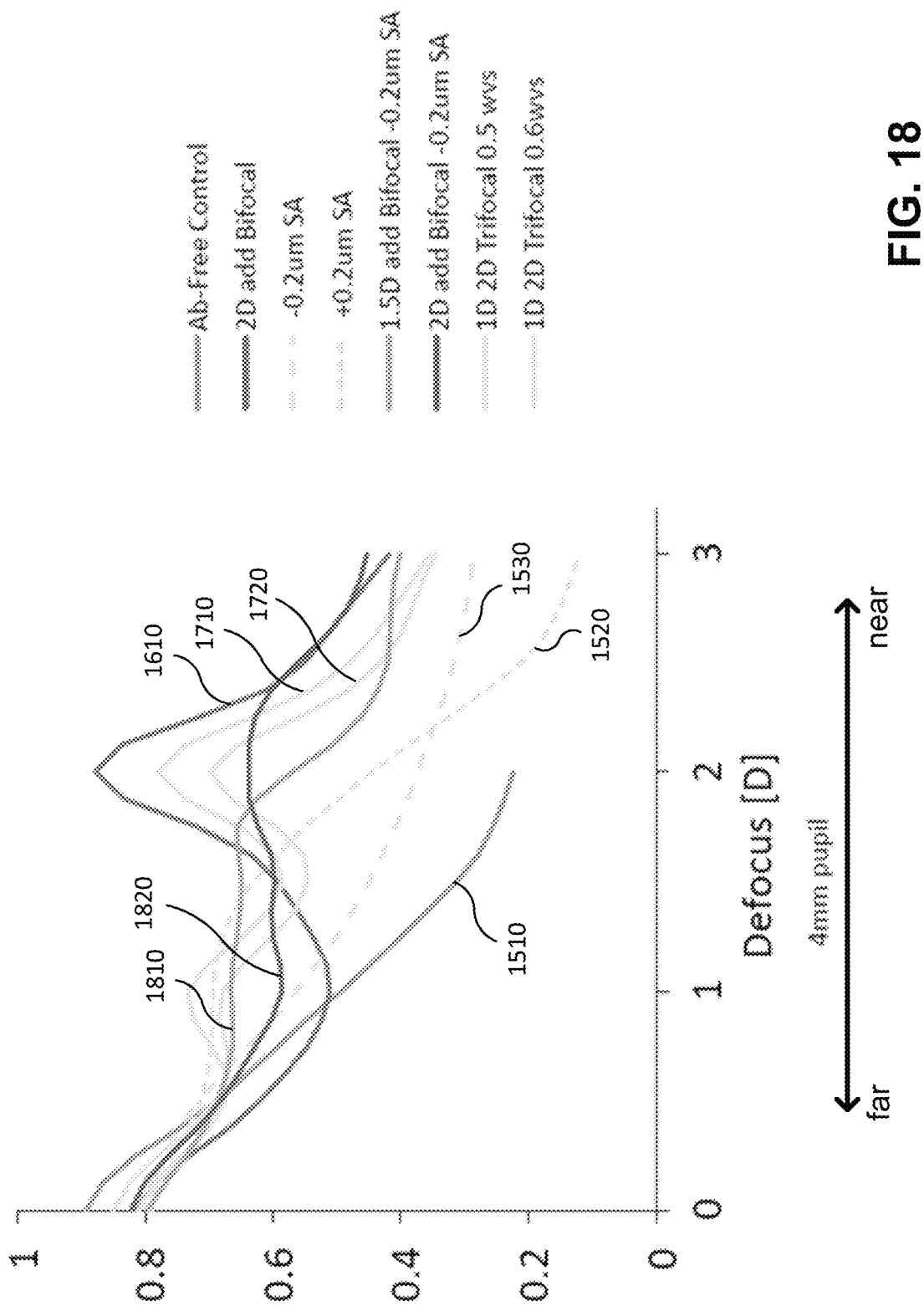
FIG. 18 illustrates a graph including a number of the previously described lines as well as lines corresponding to bifocals with spherical aberrations.

FIG. 18A illustrates a graph including a number of the previously described lines as well as lines 1810, 1820 corresponding phase-wrapped wavefronts (at 0.5 waves) including both defocus (of 1.5 diopters and 2.0 diopters, respectively) and spherical aberration. The line 1810 corresponds to a 1.5-diopter bifocal with a −0.2 µm spherical aberration. The line 1820 corresponds to a 2-diopter bifocal with a −0.2 µm spherical aberration. As shown in FIG. 18, the lines 1810 and 1820 provide image quality that is generally high and consistent across a large range of vision. For example, the line 1810 provides relatively high image quality up to around 2 diopters, with image quality for a large portion of this range being relatively constant. Similarly, the line 1820 provides high image quality up to about 2.5 diopters, again remaining relatively constant for much of this range (but with a slight dip). By contrast, the other lines all exhibit sharp drop-offs in image quality at one or more points along this range.

Figure 19A:
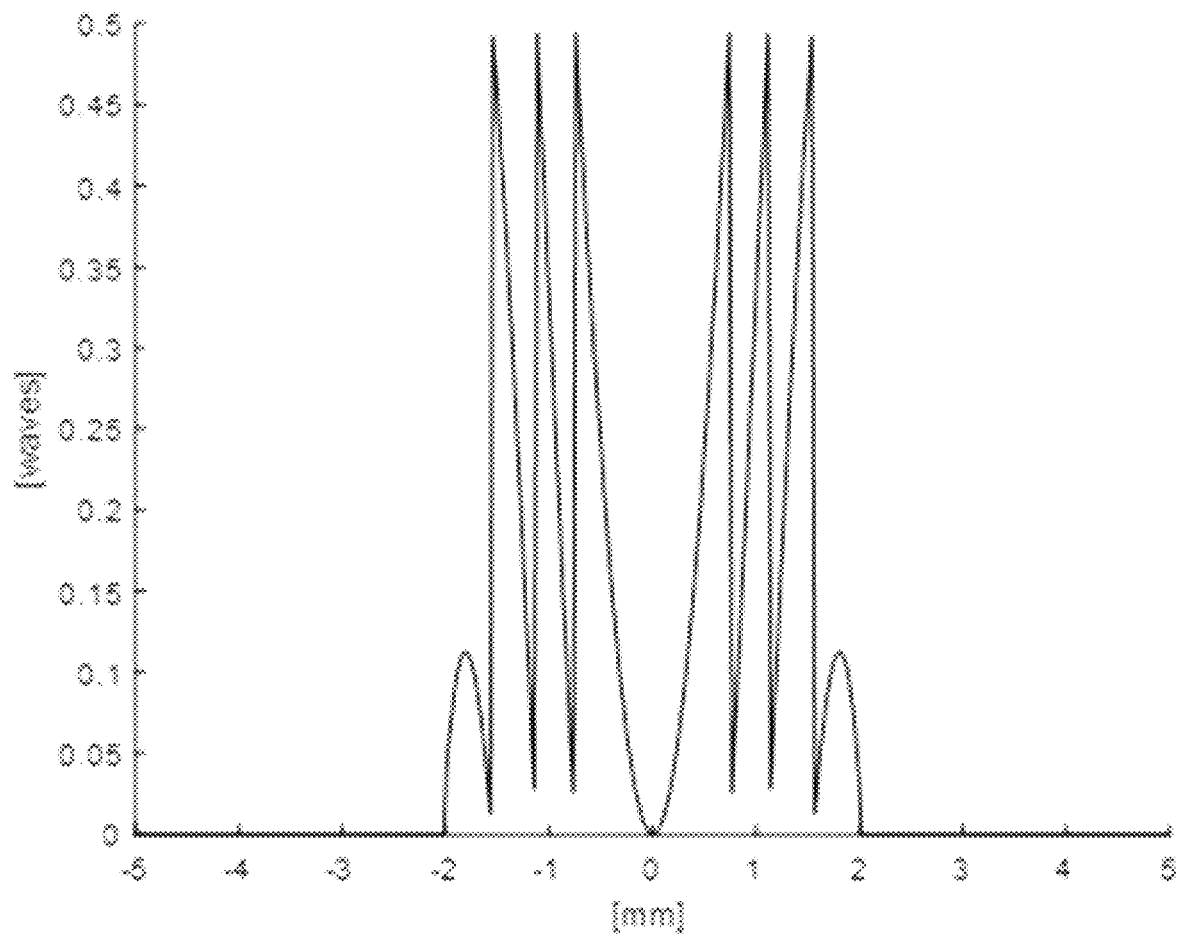
FIGS. 19A-19B illustrate cross-sections of the wavefronts corresponding to particular lines of FIG. 18.
Figure 19B:
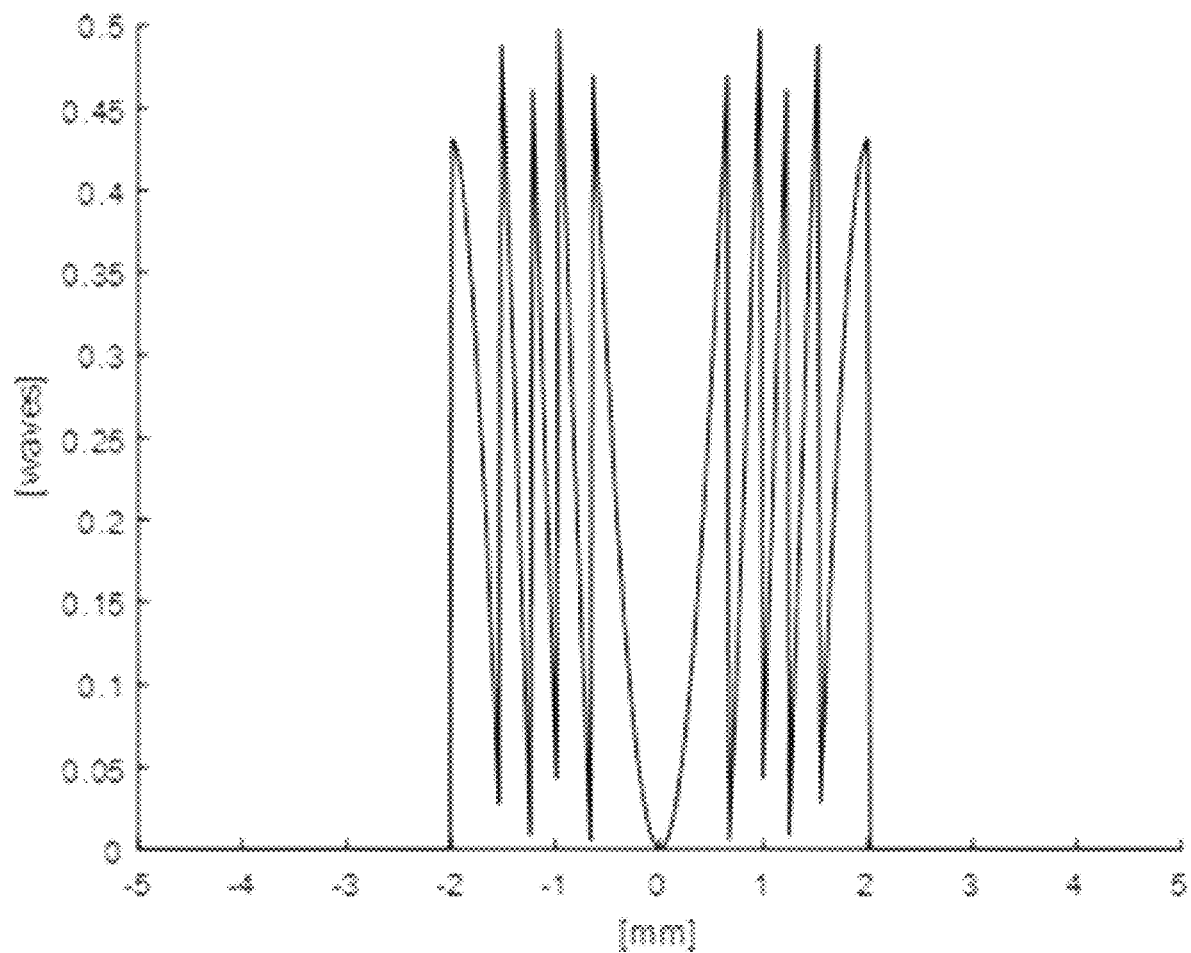

FIGS. 19A-19B illustrate cross-sections of the wavefronts corresponding to the lines 1810 and 1820 of FIG. 18. FIG. 19A corresponds to the line 1810 (1.5-diopter bifocal with a −0.2 µm spherical aberration) and FIG. 19B corresponds to the line 1820 (2-diopter bifocal with a −0.2 µm spherical aberration). As shown, these wavefronts have been phase-wrapped to have a phase height of 0.5 waves.

In some embodiments, the wavefronts may be phase wrapped as described previously. Any suitable phase height may be predetermined for the phase wrapping. In some embodiments, the phase height may be less than 1 wave. For example, a wavefront may be phase wrapped to 0.5 waves or 0.6 waves. As previously discussed, the phase height chosen for phase wrapping affects how light energy is distributed between near, intermediate, and far vision. For example, referencing the example graph in FIG. 7, at a phase height of 0.5 waves, light is equally distributed between near and far vision. As phase height is increased toward 1 wave, more of the light is distributed toward near vision than toward far vision. By contrast, as phase height is decreased toward 0 waves, more of the light is distributed toward far vision than toward near vision. A suitable phase height may be determined for the patient based on, for example, the "visual diet" of the patient as explained previously.

FIG. 20 is a table showing example wavefronts that may be implemented for different stages of presbyopia. As previously explained, presbyopia typically progresses with age, and patients can be characterized broadly as early presbyopes, mid presbyopes, and advanced presbyopes. As previously expressed, any suitable wavefront may be implemented by the described system to form a necessary ophthalmic lens. Some example wavefront characteristics for each stage are noted in FIG. 20. Using an energy source (e.g., a laser), optical structures may be formed in an ophthalmic lens (e.g., subsurface optical structures within the ophthalmic lens) to implement any suitable wavefront so as to correct a patient's vision as desired.

In some embodiments, these implementations may be phased in as presbyopia progresses. For example, an early presbyope patient may be treated with an ophthalmic lens implementing a wavefront suitable for early presbyopes. The same patient may later get a further treatment suitable for a mid presbyope once the patient's presbyopia has progressed to that stage. Similarly, the same patient may later get a further treatment suitably for an advanced presbyope once the patient's presbyopia has progressed to that stage. The systems and methods described herein are advantageous in that they allow this phasing in approach even in corneal or IOL ophthalmic lenses. For example, a patient with an IOL for early presbyopia can get a further treatment for mid or advanced presbyopia without needing a new IOL implant surgery. Instead, an energy system (e.g., a laser system) can simply modify the refractive index of the IOL as needed to implement a suitable wavefront.

FIG. 21 illustrates an example method 2100 for generating parameters for forming a subsurface optical structure in an ophthalmic lens for correcting presbyopia in a patient. The method may include, at step 2110, generating a first phase-wrapped wavefront corresponding to a first optical structure configured to cause the ophthalmic lens to diffract light to multiple focal points, wherein the first phase-wrapped wavefront is a wavefront having a first predetermined phase height less than 1 wave. The first phase-wrapped wavefront may be generated based on an optical prescription for the patient, where the optical prescription includes one or more prescription parameters for refracting light directed at a retina of the patient so as to improve vision. From this optical prescription, a first variable wavefront may be generated, wherein the first variable wavefront comprises at least one portion that has a phase height greater than 1 wave. This variable wavefront may then be collapsed to the first predetermined phase height to generate the first phase-wrapped wavefront. At step 2120, the method may include generating a first spherical wavefront configured to cause a first spherical aberration in the ophthalmic lens. The first spherical wavefront may also be based on the first optical prescription, and may be generated based on simulations of image quality metrics that would result from combining the first spherical wavefront with the first phase-wrapped wavefront. Optimal spherical and phase-wrapped wavefronts may be determined based on the simulations, in light of the patient's lifestyle or "visual diet" as explained above. At step 2130, the method may include generating, based on the first phase-wrapped wavefront and the first spherical wavefront, energy output parameters for forming a first subsurface optical structure in the ophthalmic lens using an energy source, wherein the first subsurface optical structure is configured to correct presbyopia with an extended depth of focus that allows for increased intermediate vision quality.

Particular embodiments may repeat one or more steps of the method of FIG. 21, where appropriate. Although this disclosure describes and illustrates particular steps of the method of FIG. 21 as occurring in a particular order, this disclosure contemplates any suitable steps of the method of FIG. 21 occurring in any suitable order. Moreover, although this disclosure describes and illustrates an example method for generating parameters for forming a subsurface optical structure in an ophthalmic lens for correcting presbyopia in a patient, including the particular steps of the method of FIG. 21, this disclosure contemplates any suitable method for generating parameters for forming a subsurface optical structure in an ophthalmic lens for correcting presbyopia in a patient, including any suitable steps, which may include all, some, or none of the steps of the method of FIG. 21, where appropriate. Furthermore, although this disclosure describes and illustrates particular components, devices, or systems carrying out particular steps of the method of FIG. 21, this disclosure contemplates any suitable combination of any suitable components, devices, or systems carrying out any suitable steps of the method of FIG. 21.

Adjusting for Implementation Limitations

A design phase-wrapped wavefront, as an abstract construct, can have vertical steps with infinitely abrupt changes in wavefront slope as described herein. Implementation of the design phase-wrapped wavefront in an artificial or biological optical material, however, can result in differences between the resulting optical correction and the optical correction corresponding to the design phase-wrapped wavefront. The resulting optical differences can result from what is referred to herein as a low-pass filtering of the design phase-wrapped wavefront. The low-pass filtering of the design phase-wrapped wavefront can have many causes including, but not limited to, the size of the laser point spread function, the volumes of the laser induced refractive index changes (LIRIC) in the artificial or biological optical material, and/or post-LIRIC changes in the artificial or biological optical material (e.g., biological remodeling, swelling, etc.).

Figure 22:
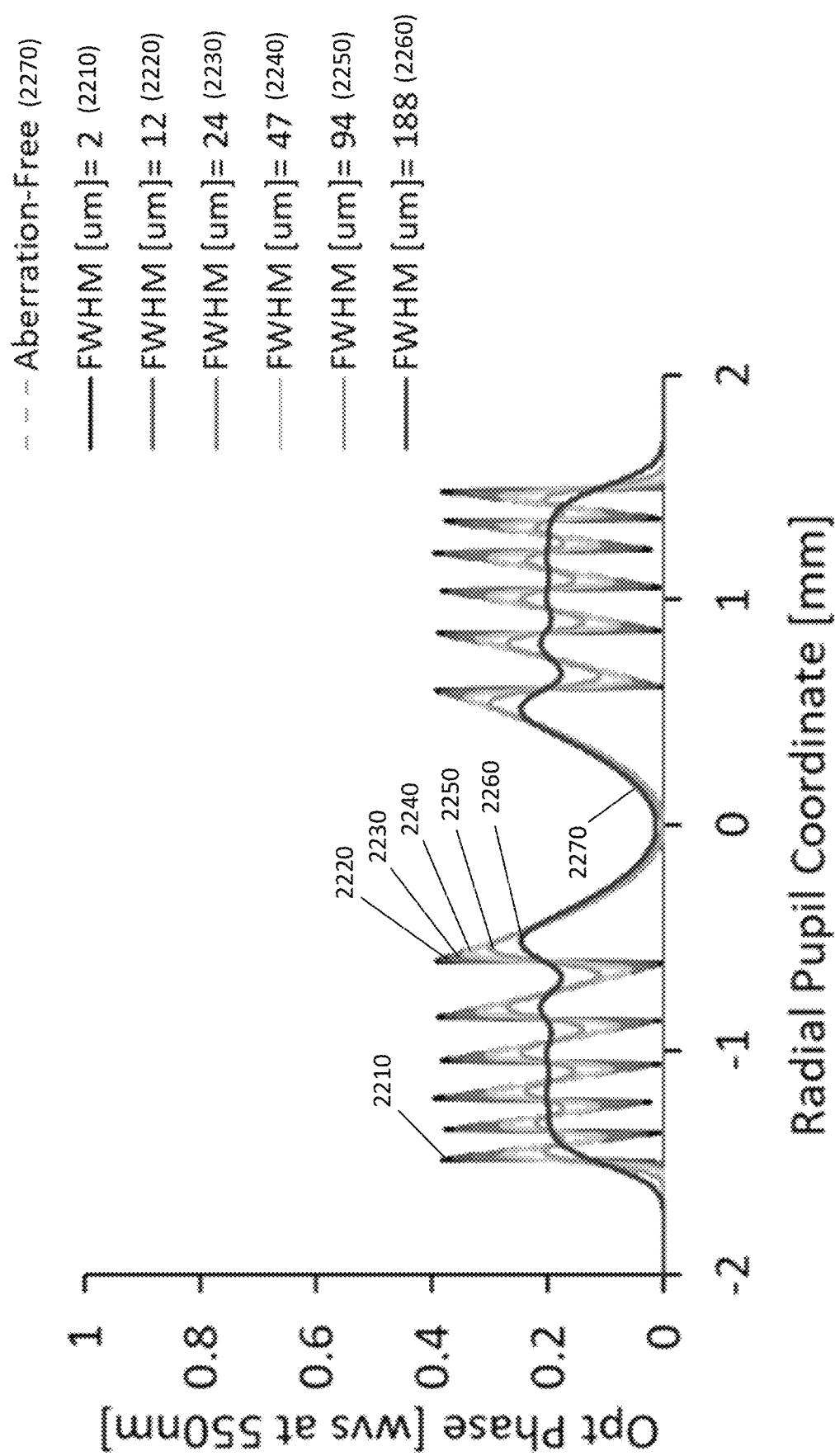
FIG. 22 illustrates simulated resulting phase-wrapped wavefronts for a design 0.4 wave height phase-wrapped wavefront due to practical limitations associated with inducing the design 0.4 wave height phase-wrapped wavefront in an artificial or biological optical material.
Figure 23:
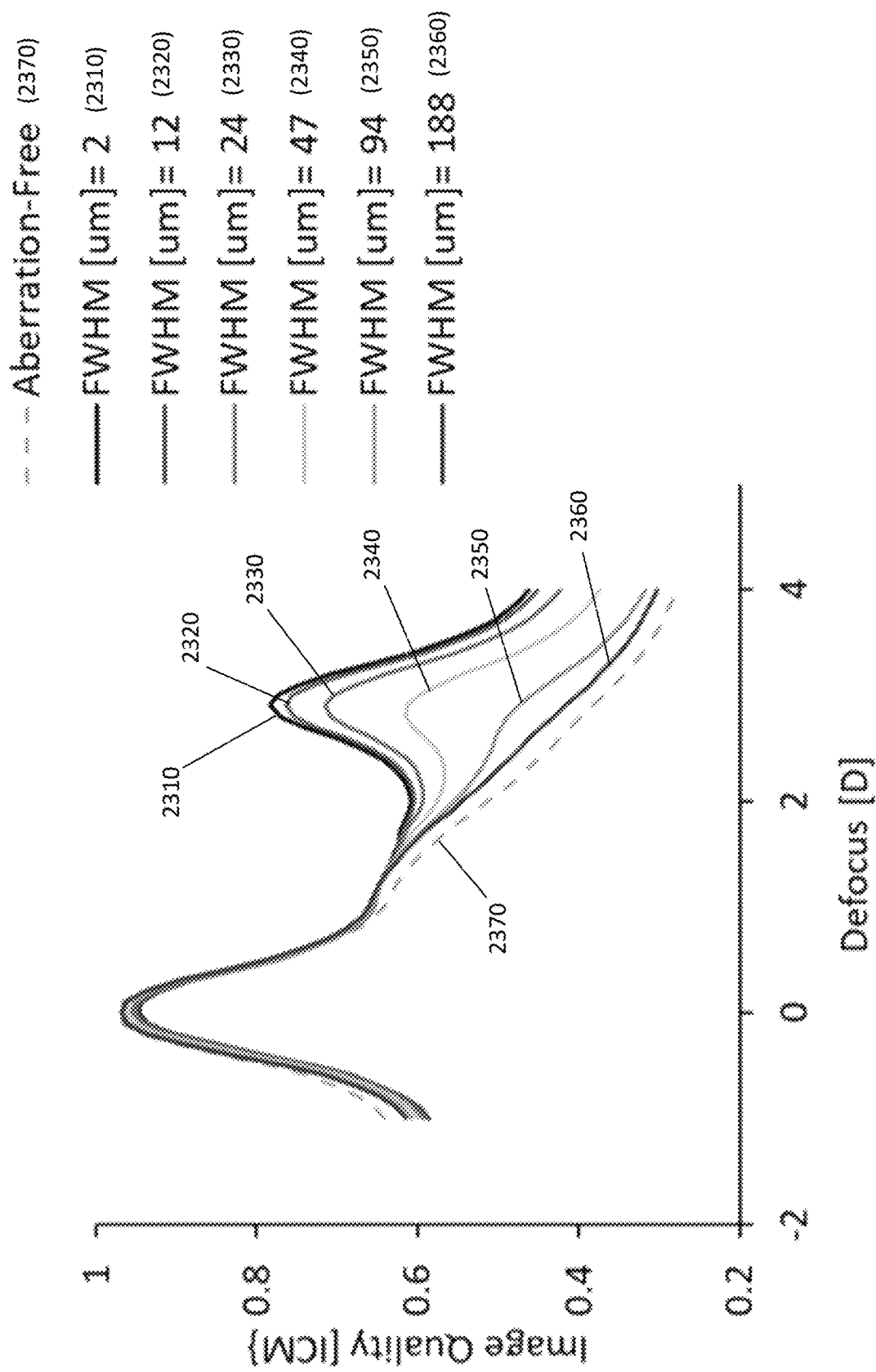
FIG. 23 illustrates simulated resulting through-focus retinal image quality for the simulated resulting phase-wrapped wavefronts of FIG. 22.

To assess the impact of the low-pass filtering, simulation of through-focus retinal image quality (RIQ) (monochromatic at 550 nm, 3 mm pupil diameter, 3 diopter add-power diffractive multifocal wavefront, Image Convolution Metric) was simulated using Matlab for different amounts of low-pass filtering with a Gaussian function (full width at half maximum (FWHM) from 2 um to 188 um). FIG. 22 illustrates simulated resulting phase-wrapped wavefronts 2210, 2220, 2230, 2240, 2250, 2260, 2270 for an intended 0.4 wave height phase-wrapped wavefront due to the impact of the different amounts of the low-pass filtering. As illustrated, the peak wave heights of the resulting effective phase-wrapped wavefront are increasingly reduced in magnitude from the design 0.4 wave height for increasing magnitudes of the low-pass filtering. FIG. 23 illustrates simulated resulting through-focus (RIQ) 2310, 2320, 2330, 2340, 2350, 2360, 2370 for the simulated resulting phase-wrapped wavefronts of FIG. 22. The simulated resulting through-focus RIQs show increasing reduction in near visual benefit and near vision RIQ, and increases distance RIQ for increasing magnitudes of the low-pass filtering, ultimately reverting to the pre-treatment RIQ at the highest magnitude of the low-pass filtering.

Figure 24:
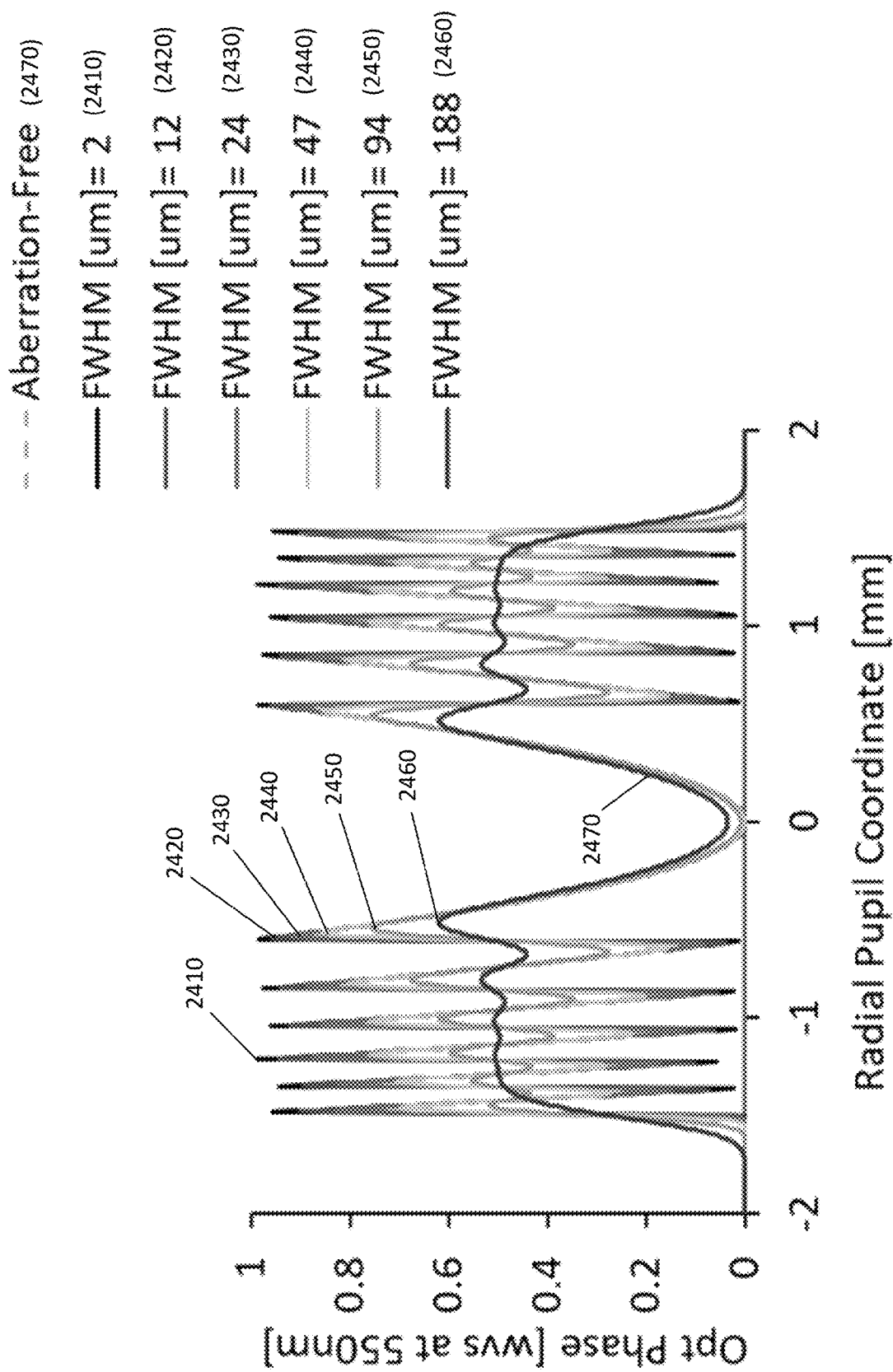
FIG. 24 illustrates simulated resulting phase-wrapped wavefronts for a scaled-up version of the 0.4 wave height phase-wrapped wavefront of FIG. 22.
Figure 25:
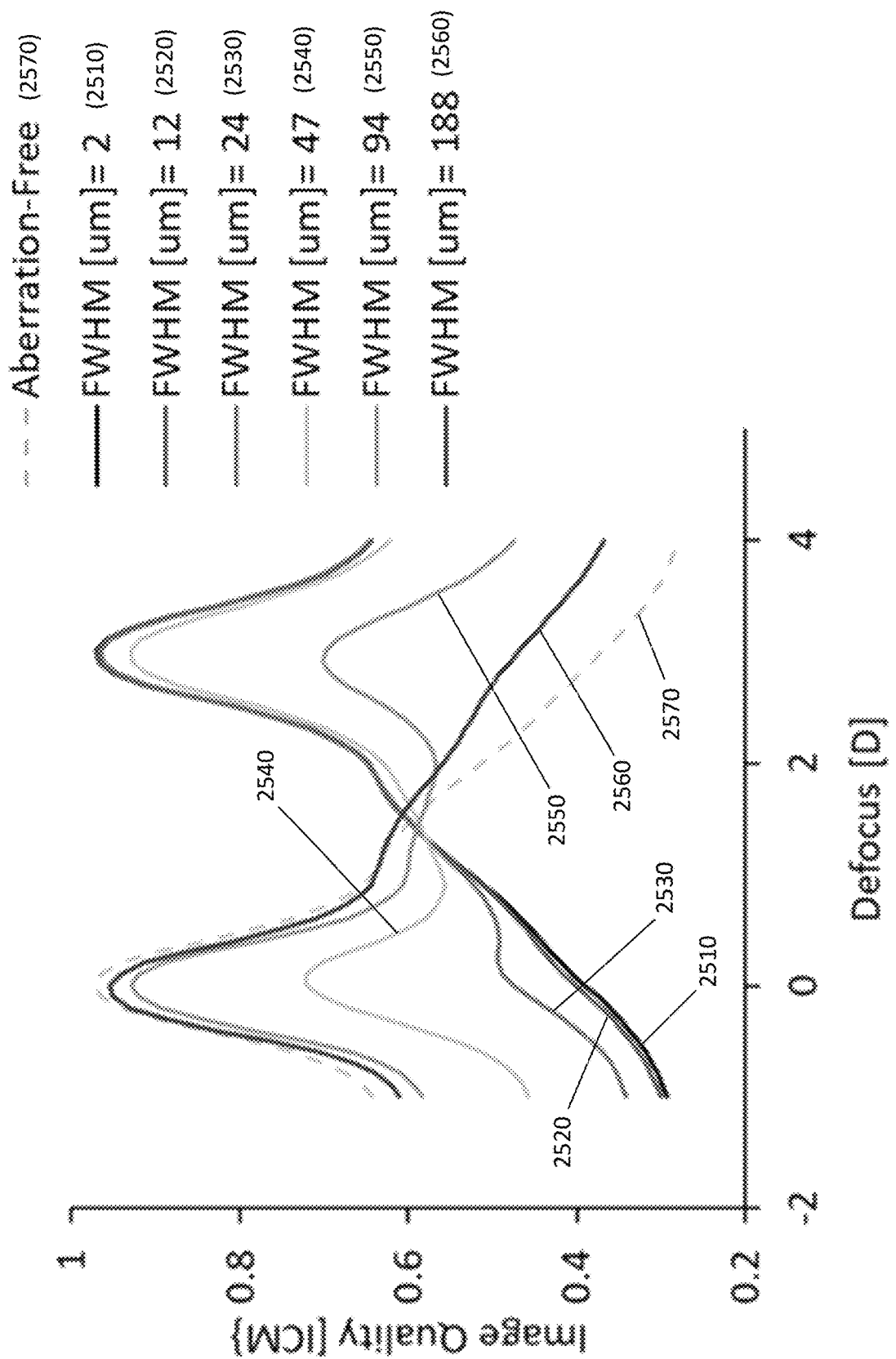
FIG. 25 illustrates simulated resulting through-focus retinal image quality for the simulated resulting phase-wrapped wavefronts of FIG. 24.
Figure 26:
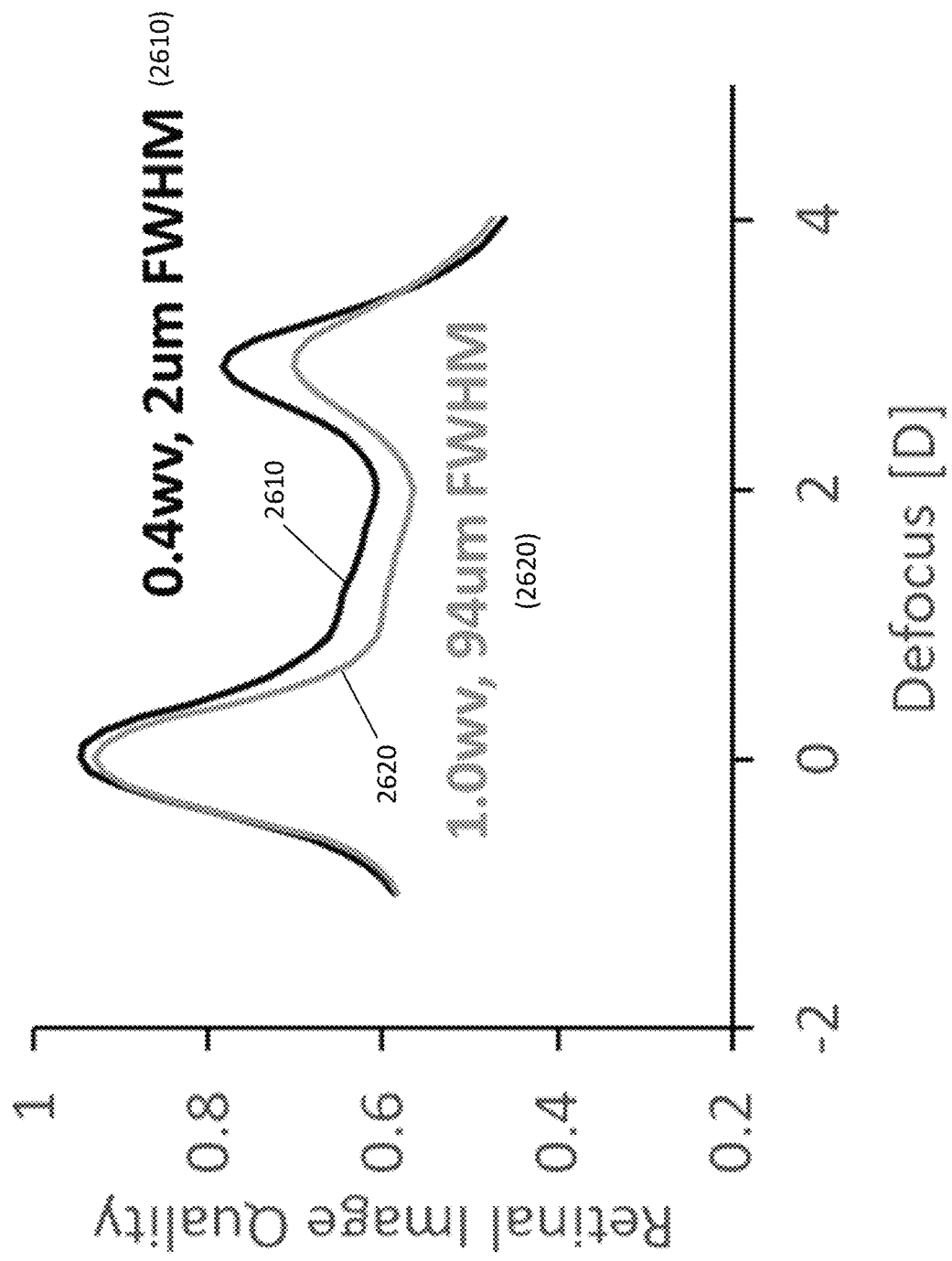
FIG. 26 shows simulated resulting through-focus retinal image qualities illustrating that near visual benefit can be recovered by scaling a design wavefront height.

To compensate for the impact of the low-pass filtering on the through-focus (RIQ), the design peak wave height can be increased or scaled by a suitable amount. For example, FIG. 24 illustrates simulated resulting phase-wrapped wavefronts 2410, 2420, 2430, 2440, 2450, 2460, 2470 for a scaled-up version of the design 0.4 wave height phase-wrapped wavefront of FIG. 22. The scaled-up version of the design 0.4 wave height phase-wrapped wavefront has been scaled up by (1.0/0.4) to increase the wavefront peaks from 0.4 wave to 1.0 wave. FIG. 24 illustrates simulated resulting phase-wrapped wavefronts for the scaled-up version of the design 0.4 wave height phase-wrapped wavefront due to the impact of the different amounts of the low-pass filtering. As illustrated, the peak wave heights of the resulting effective phase-wrapped wavefront are increasingly reduced in magnitude from the resulting 1.0 wave height for increasing magnitudes of the low-pass filtering. FIG. 25 illustrates simulated resulting through-focus (RIQ) 2510, 2520, 2530, 2540, 2550, 2560, 2570 for the simulated resulting phase-wrapped wavefronts of FIG. 24. The simulated resulting through-focus RIQs for the scaled-up version show increased near visual benefit and near RIQ relative to the design 0.4 wave height phase-wrapped wavefront for the different amounts of the low-pass filtering. FIG. 26 shows simulated resulting through-focus retinal image qualities illustrating that near visual benefit can be recovered by scaling the design wavefront height. As illustrated, the scaled-up version of the design 0.4 wave height phase-wrapped wavefront has a comparable through focus RIQ 2620 at a higher level of low-pass filtering (94 um FMHM) relative to the design 0.4 wave height phase-wrapped wavefront 2610 at a lower level of low-pass filtering (2 um FWHM). Accordingly, scaling up of a design phase-wrapped wavefront can be used to compensate for the impact of resulting low-pass filtering associated with physically inducing the phase-wrapped wavefront in an artificial or biological optical material.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of modifying a lens to improve image quality of a patient with presbyopia, the method comprising:
    inducing changes in refractive index of subsurface volumes of the lens to form a first subsurface optical structure configured to induce a first wavefront correction configured to increase depth of focus and intermediate vision quality for a patient when the patient has a first range of accommodation; and
    inducing changes in refractive index of subsurface volumes of the lens to form a second subsurface optical structure, wherein the first subsurface optical structure and the second subsurface optical structure, in combination, are configured to induce a second wavefront correction configured to increase depth of focus and intermediate vision quality for the patient when the patient has a second range of accommodation less than the first range of accommodation.

2. The method of claim 1, wherein the lens is a native crystalline lens of the patient, an intraocular lens implanted in the patient, or a cornea of the patient.

3. The method of claim 1, wherein:
    the first wavefront correction provides a first bifocal correction having a first diopter add power; and
    the first wavefront correction and the second wavefront correction, in combination, provide a second bifocal correction having a second diopter add power greater than the first diopter add power.

4. The method of claim 3, wherein the first wavefront correction and the second wavefront correction, in combination, further induce a spherical aberration.

5. The method of claim 4, wherein the spherical aberration is about −0.2 µm.

6. The method of claim 4, wherein the spherical aberration is about 0.2 µm.

7. The method of claim 1, wherein:
    the first wavefront correction provides a first trifocal correction having first trifocal add powers; and
    the first wavefront correction and the second wavefront correction, in combination, provide a second trifocal correction having second trifocal add powers greater than the first trifocal add powers.

8. The method of claim 7, wherein the first wavefront correction and the second wavefront correction, in combination, further induce a spherical aberration.

9. The method of claim 8, wherein the spherical aberration is about −0.2 um.

10. The method of claim 8, wherein the spherical aberration is about 0.2 um.

11. The method of claim 7, wherein:
    the first wavefront correction further induces a first spherical aberration; and
    the first wavefront correction and the second wavefront correction, in combination, further induce a second spherical aberration.

12. The method of claim 1, wherein:
    the first wavefront correction induces a first spherical aberration; and
    the first wavefront correction and the second wavefront correction, in combination, provide a bifocal correction and induce a second spherical aberration.

13. The method of claim 1, wherein:
    the first wavefront correction induces a first spherical aberration; and
    the first wavefront correction and the second wavefront correction, in combination, provide a trifocal correction and induce a second spherical aberration.

14. The method of claim 1, wherein the first wavefront correction is configured to diffract light to multiple focal points based on a first phase-wrapped wavefront having a first predetermined phase height not equal to 1 wave.

15. The method of claim 14, wherein the first predetermined phase height is between about 0.5 to 0.6 waves.

16. The method of claim 14, wherein the second wavefront correction is configured to diffract light to multiple focal points based on a second phase-wrapped wavefront having a second predetermined phase height not equal to 1 wave.

17. The method of claim 16, wherein the first predetermined phase height is between about 0.5 to 0.6 waves.

18. The method of claim 1, wherein the inducing of the changes in refractive index of subsurface volumes of the lens to form the first subsurface optical structure and the second subsurface optical structure comprises directing energy pulses into the lens.

* * * * *